(12) United States Patent
Brown et al.

(10) Patent No.: US 11,596,718 B2
(45) Date of Patent: *Mar. 7, 2023

(54) LAYER BY LAYER COATED MESH FOR LOCAL RELEASE OF BIO-ACTIVE PROTEINS

(71) Applicant: UNIVERSITY OF PITTSBURGH—OF THE COMMONWEALTH SYSTEM OF HIGHER EDUCATION, Pittsburgh, PA (US)

(72) Inventors: Bryan Nicklaus Brown, Pittsburgh, PA (US); Daniel Jordi Hachim Diaz, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 209 days.

This patent is subject to a terminal disclaimer.

(21) Appl. No.: 17/111,704

(22) Filed: Dec. 4, 2020

(65) Prior Publication Data

US 2021/0106731 A1   Apr. 15, 2021

Related U.S. Application Data

(63) Continuation of application No. 16/741,269, filed on Jan. 13, 2020, now Pat. No. 10,888,641, which is a (Continued)

(51) Int. Cl.
  *A61L 27/54*   (2006.01)
  *A61L 29/16*   (2006.01)
  (Continued)

(52) U.S. Cl.
  CPC ........ *A61L 31/048* (2013.01); *A61K 38/2026* (2013.01); *A61L 15/44* (2013.01);
  (Continued)

(58) Field of Classification Search
  CPC ...... A61L 31/048; A61L 15/44; A61L 17/005; A61L 17/145; A61L 2420/02;
  (Continued)

(56) References Cited

U.S. PATENT DOCUMENTS 3,276,448 A      10/1966  Kronenthal
10,576,187 B2 *   3/2020  Brown ................... A61L 15/44
                         (Continued)

FOREIGN PATENT DOCUMENTS

WO   WO 2008/107483 A3   9/2008
WO   WO 2013/046057 A1   4/2013

OTHER PUBLICATIONS

U.S. Appl. No. 16/741,269 (U.S. Pat. No. 10,888,641), filed Jan. 13, 2020 (Jan. 12, 2021).

(Continued)

*Primary Examiner* — Ernst V Arnold
(74) *Attorney, Agent, or Firm* — Baker Botts L.L.P.

(57) ABSTRACT

The present invention relates to biomaterials coated with an active agent eluting coating, wherein implantation of the coated biomaterial results in reduced implant-related complications and/or improved integration of the biomaterial into the host tissue and further relates to kits containing the coated biomaterial. The present invention also relates to methods and kits for coating the biomaterial. It is based, at least in part, on the discovery that biomaterial coated with a cytokine eluting coating resulted in the shift of early stage macrophage polarization that were associated with positive (Continued)

Figure 1:
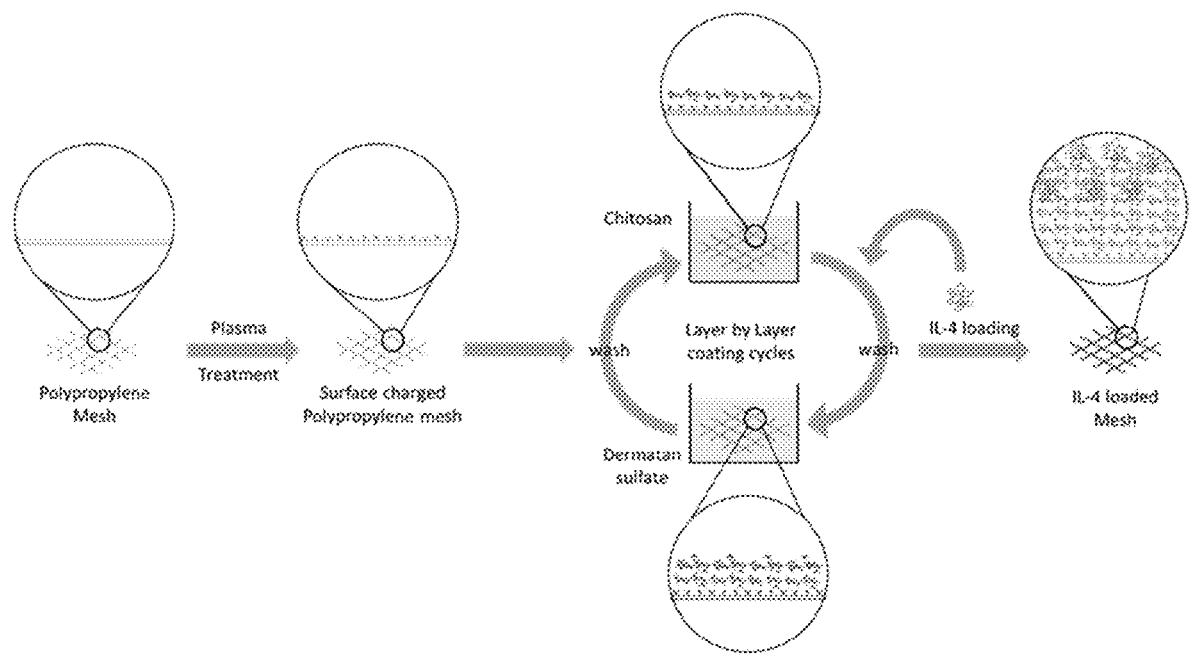

long-term effects such as minimized capsule formation and improved tissue quality and composition as compared to uncoated biomaterials.

20 Claims, 14 Drawing Sheets

Related U.S. Application Data continuation of application No. 15/459,993, filed on Mar. 15, 2017, now Pat. No. 10,576,187.

(60) Provisional application No. 62/308,574, filed on Mar. 15, 2016.

(51) Int. Cl.
| | | |
|---|---|---|
| *A61L 31/16* | (2006.01) | |
| *A61K 38/20* | (2006.01) | |
| *A61L 31/04* | (2006.01) | |
| *A61L 31/10* | (2006.01) | |
| *B05D 7/00* | (2006.01) | |
| *A61M 31/00* | (2006.01) | |
| *A61L 17/14* | (2006.01) | |
| *A61L 15/44* | (2006.01) | |
| *A61L 27/34* | (2006.01) | |
| *A61L 29/08* | (2006.01) | |
| *A61L 17/00* | (2006.01) | |
| *A61F 2/00* | (2006.01) | |
| *B05D 1/36* | (2006.01) | |
| *B05D 1/18* | (2006.01) | |

(52) U.S. Cl.
CPC .......... *A61L 17/005* (2013.01); *A61L 17/145* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *A61M 31/002* (2013.01); *B05D 7/56* (2013.01); *A61F 2/0063* (2013.01); *A61F 2210/0076* (2013.01); *A61F 2250/0067* (2013.01); *A61L 2420/02* (2013.01); *A61L 2420/08* (2013.01); *B05D 1/18* (2013.01); *B05D 1/36* (2013.01)

(58) Field of Classification Search
CPC ...... A61L 2420/08; A61L 27/34; A61L 27/54; A61L 29/085; A61L 29/16; A61L 31/10; A61L 31/16; C08L 23/10; A61F 2210/0076; A61F 2250/0076; A61F 2250/0067; A61F 2/0063; A61K 38/2026; A61M 31/002; B05D 1/18; B05D 1/36; B05D 7/56
See application file for complete search history.

(56) References Cited

U.S. PATENT DOCUMENTS

| | | | | |
|---|---|---|---|---|
| 10,888,641 | B2* | 1/2021 | Brown | ................. A61L 29/085 |
| 2009/0060971 | A1 | 3/2009 | McKay | |
| 2009/0088679 | A1 | 4/2009 | Wood et al. | |

OTHER PUBLICATIONS

U.S. Appl. No. 15/459,993 (U.S. Pat. No. 10,576,187), filed Mar. 15, 2017 (Mar. 3, 2020).
U.S. Appl. No. 16/741,269, Dec. 10, 2020 Issue Fee Payment.
U.S. Appl. No. 16/741,269, Sep. 22, 2020 Notice of Allowance.
U.S. Appl. No. 16/741,269, Aug. 11, 2020 Response to Restriction Requirement.
U.S. Appl. No. 16/741,269, Jun. 24, 2020 Restriction Requirement.
U.S. Appl. No. 15/459,993, Jan. 21, 2020 Issue Fee Payment.
U.S. Appl. No. 15/459,993, Oct. 22, 2019 Notice of Allowance.
U.S. Appl. No. 15/459,993, Sep. 26, 2019 Applicant Initiated Interview Summary.
U.S. Appl. No. 15/459,993, Sep. 26, 2019 Amendment and Request for Continued Examination (RCE).
U.S. Appl. No. 15/459,993, Jul. 18, 2019 Pre-Brief Appeal Conference Decision.
U.S. Appl. No. 15/459,993, Jun. 26, 2019 Notice of Appeal Filed and Pre-Brief Conference Request.
U.S. Appl. No. 15/459,993, Mar. 27, 2019 Non-Final Office Action.
U.S. Appl. No. 15/459,993, Mar. 15, 2019 Request for Continued Examination (RCE).
U.S. Appl. No. 15/459,993, Feb. 26, 2019 Advisory Action.
U.S. Appl. No. 15/459,993, Feb. 15, 2019 Response to Final Office Action.
U.S. Appl. No. 15/459,993, Dec. 17, 2018 Final Office Action.
U.S. Appl. No. 15/459,993, Nov. 12, 2018 Response to Non-Final Office Action.
U.S. Appl. No. 15/459,993, Sep. 11, 2018 Non-Final Office Action.
U.S. Appl. No. 15/459,993, Aug. 24, 2018 Amendment and Request for Continued Examination (RCE).
U.S. Appl. No. 15/459,993, Jul. 10, 2018 Advisory Action.
U.S. Appl. No. 15/459,993, Jul. 10, 2018 Applicant Initiated Interview Summary.
U.S. Appl. No. 15/459,993, Jun. 26, 2018 Response to Final Office Action.
U.S. Appl. No. 15/459,993, Apr. 26, 2018 Final Office Action.
U.S. Appl. No. 15/459,993, Mar. 22, 2018 Response to Non-Final Office Action.
U.S. Appl. No. 15/459,993, Dec. 22, 2017 Non-Final Office Action.
U.S. Appl. No. 15/459,993, Dec. 4, 2017 Response to Restriction Requirement.
U.S. Appl. No. 15/459,993, Oct. 3, 2017 Restriction Requirement.
Ai et al., "Biomedical Applications of Electrostatic Layer-by-Layer Nano-Assembly of Polymers, Enzymes, and Nanoparticles," Cell Biochem Biophys 39:23-43 (2003).
Anderson et al., "Foreign body reaction to biomaterials," Semin Immunol 20:86-100 (2008).
Anderson et al., "Phenotypic dichotomies in the foreign body reaction," Biomaterials 28:5114-5120 (2007).
Aumsuwan et al., "Covalent Attachment of Multilayers on Poly(tetrafluoroethylene) Surfaces," Langmuir 27:11106-11110 (2011).
Badylak et al., "Immune Response to Biologic Scaffold Materials," Semin Immunol 20(2):109-116 (2008).
Barbeck et al., "Heterogeneity of biomaterial-induced multinucleated giant cells: Possible importance for the regeneration process?" J Biomed Mater Res Part A 104A:413-418 (2016).
Barron et al., "Fibrosis is regulated by Th2 and Th17 responses and by dynamic interactions between fibroblasts and macrophages," Am. J. Physiol. Gastrointest. Liver Physiol. 300:G723-G728 (2011).
Borges et al., "Molecular Interactions Driving the Layer-by-Layer Assembly of Multilayers," Chem Rev 114:8883-8942 (2014).
Brown et al., "Characterization of the host inflammatory response following implantation of prolapse mesh in rhesus macaque," Am J Obstet Gynecol 213:668.e1-10 (2015).
Brown et al., "Expanded applications, shifting paradigms and an improved understanding of host-biomaterial interactions," Acta Biomaterialia 9:4948-4955 (2013).
Brown et al., "Macrophage phenotype and remodeling outcomes in response to biologic scaffolds with and without a cellular component," Biomaterials 30:1482-1491 (2009).
Brown et al., "Macrophage Phenotype as a Predictor of Constructive Remodeling following the Implantation of Biologically Derived Surgical Mesh Materials," Acta Biomater 8(3):978-987 (2012).
Brown et al., "Macrophage polarization: An opportunity for improved outcomes in biomaterials and regenerative medicine," Biomaterials 33(15):3792-3802 (2012).
Brown et al., "Rethinking regenerative medicine: a macrophage-centered approach," Front Immunol 5:510 (2014).

(56) References Cited

OTHER PUBLICATIONS

Bryers et al., "Engineering Biomaterials to Integrate and Heal: The Biocompatibility Paradigm Shifts," Biotechnol Bioeng 109(8):1898-1911 (2012).

Cervigni et al., "Collagen-coated polypropylene mesh in vaginal prolapse surgery: an observational study," Eur J Obstet Gynecol Reprod Biol. 156:223-227 (2011).

Choi et al., "Layer-by-layer assembly of multilayer films for controlled drug release," Arch. Pharm. Res. 37:79-87 (2014).

Den Dekker et al., "Monocyte Cell Surface Glycosaminoglycans Positively Modulate IL-4-Induced Differentiation toward Dendritic Cells," J Immunol 180:3680-3688 (2008).

Ellington et al., "Indications, Contraindications, and Complications of Mesh in Surgical Treatment of Pelvic Organ Prolapse," Clin Obstet Gynecol. 56(2):276-288 (2013).

Faulk et al., "ECM hydrogel coating mitigates the chronic inflammatory response to polypropylene mesh," Biomaterials 35:8585-8595 (2014).

Fearing et al., "In vitro response of macrophage polarization to a keratin biomaterial," Acta Biomaterialia 10:3136-3144 (2014).

Freytes et al., "Optimizing Dynamic Interactions between a Cardiac Patch and Inflammatory Host Cells," Cells Tissues Organs 195:171-182 (2012).

Goodman, "Wear particles, periprosthetic osteolysis and the immune system," Biomaterials 28:5044-5048 (2007).

Guo et al., "Substrate Modulus of 3D-Printed Scaffolds Regulates the Regenerative Response in Subcutaneous Implants through the Macrophage Phenotype and Wnt Signaling," Biomaterials 73:85-95 (2015).

Hachim D, LoPresti ST, Brown BN. Development of a Cytokine-Loaded Layer by Layer Coating on Polypropylene Meshes to Modulate Macrophage Polarization at the Tissue-Implant Interface. Society for Biomaterials (Abstract), Apr. 2015, Charlotte, NC.

Hachim et al., "Development of a Cytokine-Loaded Layer by Layer Coating on Polypropylene Meshes to Modulate Macrophage Polarization at the Tissue-Implant Interface," Society for Biomaterials (Presentation), Apr. 2015, Charlotte, NC.

Hachim et al., "Modulation of Macrophage Polarization at the Tissue-Implant Interface by Local Release of IL-4 from a Nanometer Thickness Coating on Polypropylene Meshes," Regenerative Medicine Workshop (Poster), May 2015. Hilton Head, NC.

Hachim et al., "Modulation of Macrophage Polarization at the Tissue-Implant Interface by Local Release of IL-4 from a Nanometer Thickness Coating on Polypropylene Meshes," Regenerative Medicine Workshop (Abstract), May 2015. Hilton Head, NC.

Hachim et al., "Modulation of Macrophage Polarization at the Tissue-Implant Interface by Local Release of IL-4 from a Nanometer Thickness Coating on Polypropylene Meshes," Biomedical Engineering Society (Presentation), Oct. 2015, Tampa, FL.

Hachim et al., "Modulation of Macrophage Polarization at the Tissue-Implant Interface by Local Release of IL-4 from a Nanometer Thickness Coating on Polypropylene Meshes," Biomedical Engineering Society (Abstract), Oct. 2015, Tampa, FL.

Hachim et al., "Pro-remodeling Macrophage Polarization at the Tissue-Implant Interface by Local Release of IL-4 from Coated Polypropylene Meshes," TERMIS Word Conference (Poster), Sep. 2015. Boston, MA.

Hachim et al., "Pro-remodeling Macrophage Polarization at the Tissue-Implant Interface by Local Release of IL-4 from Coated Polypropylene Meshes," TERMIS Word Conference (Abstract), Sep. 2015. Boston, MA.

Ho et al., "Derivation and Characterization of Murine Alternatively Activated (M2) Macrophages," Methods Mol Biol 531:173-185 (2009).

Holt et al., "Cell-cell signaling in co-cultures of macrophages and fibroblasts," Biomaterials 31:9382-9394 (2010).

Holt et al., "Multinucleated giant cells from fibroblast cultures," Biomaterials 32:3977-3987 (2011).

Jamsen et al., "Characterization of Macrophage Polarizing Cytokines in the Aseptic Loosening of Total Hip Replacements," J. Orthop. Res. 32:1241-1246 (2014).

Jetten et al., "Wound Administration of M2-Polarized Macrophages Does Not Improve Murine Cutaneous Healing Responses," PLoS One 9(7):e102994 (2014).

Jiang et al. (Nanotechnology, Science and Applications Aug. 2009 pp. 21-27) (Year: 2009).

Jones et al., "Matrix metalloproteinases and their inhibitors in the foreign body reaction on biomaterials," J. Biomed. Mater. Res. 84A:158-166 (2008).

Keeney et al., "Mutant MCP-1 protein delivery from layer-by-layer coatings on orthopedic implants to modulate inflammatory response," Biomaterials 34:10287-10295 (2013).

Khandwekar et al., "In vivo modulation of foreign body response on polyurethane by surface entrapment technique," J Biomed Mater Res Part A 95A:413-423 (2010).

Klinge et al., "Impact of Polymer Pore Size on the Interface Scar Formation in a Rat Model," J Surg Res 103:208-214 (2002).

Kong et al., "Antimicrobial properties of chitosan and mode of action: A state of the art review," Int J Food Microbiol 144:51-63 (2010).

Lawrence et al., "Transcriptional regulation of macrophage polarization: enabling diversity with identity," Nat Rev Immunol 11:750-761 (2011).

Lee et al., "Role of Chitin and Chitinase/Chitinase-Like Proteins in Inflammation, Tissue Remodeling, and Injury," Annu Rev Physiol 73:479-501 (2011).

Li et al., "Multilayer polypeptide nanoscale coatings incorporating IL-12 for the prevention of biomedical device associated infections," Biomaterials 30(13):2552-2558 (2009).

Lin et al., "Exposure of polyethylene particles induces interferon-γ expression in a natural killer T lymphocyte and dendritic cell coculture system in vitro: A preliminary study," J. Biomed. Mater. Res. Part A 103A:71-75 (2015).

Lin et al., "NF-κB Decoy Oligodeoxynucleotide Mitigates Wear Particle-Associated Bone Loss in the Murine Continuous Infusion Model," Acta Biomater. 41:273-281 (2016).

Liu et al., "Macrophage Polarization in Inflammatory Diseases," Int J Biol Sci 10:520-529 (2014).

Liu et al., "Reduced foreign body reaction to implanted biomaterials by surface treatment with oriented osteopontin," J Biomater Sci Polym Ed 19(6):821-835 (2008).

Luo et al. (International Journal of Biological Macromolecules 2014(64):353-367) (Year: 2014).

Luzina et al., "Alternatively spliced variants of interleukin-4 promote inflammation differentially," J. Leukoc. Biol. 89:763-770 (2011).

Luzina et al., "Regulation of inflammation by interleukin-4: a review of "alternatives"," J. Leukoc. Biol. 92(4):753-764 (2012).

Macdonald et al., "Characterization of Tunable FGF-2 Releasing Polyelectrolyte Multilayers," Biomacromolecules 11:2053-2059 (2010).

Macdonald et al., "Release of a model protein from biodegradable self assembled films for surface delivery applications," J Control Release 131:228-234 (2008).

Madden et al., "Proangiogenic scaffolds as functional templates for cardiac tissue engineering," PNAS USA 107(34):15211-15216 (2010).

Mantovani et al., "Macrophage plasticity and polarization in tissue repair and remodeling," J Pathol 229:176-185 (2013).

Martinez et al., "The M1 and M2 paradigm of macrophage activation: time for reassessment," F1000Prime Rep 6:13 (2014).

Martucci et al., "Chronic fentanyl or buprenorphine infusion in the mouse: similar analgesic profile but different effects on immune responses," Pain 110:385-392 (2004).

McNally et al., "Interleukin-4 Induces Foreign Body Giant Cells from Human Monocytes/Macrophages. Differential Lymphokine Regulation of Macrophage Fusion Leads to Morphological Variants of Multinucleated Giant Cells," Am. J. Pathol. 147(5):1487-1499 (1995).

Meyers et al., "Biocompatible and Bioactive Surface Modifications for Prolonged In Vivo Efficacy," Chem Rev 112:1615-1632 (2012).

Mills, "M1 and M2 Macrophages: Oracles of Health and Disease," Crit Rev Immunol 32(6):463-488 (2012).

(56) References Cited

OTHER PUBLICATIONS

Miron et al., "OsteoMacs: Key players around bone biomaterials," Biomaterials 82:1-19 (2016).
Mokarram et al., "Effect of modulating macrophage phenotype on peripheral nerve repair," Biomaterials 33:8793-8801 (2012).
Mosser et al., "Exploring the full spectrum of macrophage activation," Nat Rev Immunol. 8(12):958-969 (2008).
Murray et al., "Obstacles and opportunities for understanding macrophage polarization," J. Leukoc. Biol. 89(4):557-563 (2011).
Murray et al., "Protective and pathogenic functions of macrophage subsets," Nat Rev Immunol. 11(11):723-737 (2011).
Nadkarni et al., "Measurement of Collagen and Smooth Muscle Cell Content in Atherosclerotic Plaques Using Polarization-Sensitive Optical Coherence Tomography," J Am Coll Cardiol 49(13):1474-1481 (2007).
Nolfi et al., "Host response to synthetic mesh in women with mesh complications," Am. J. Obstet. Gynecol. 215(2):206.e1-206.e8 (2016).
Novak et al., "Macrophage phenotypes during tissue repair," J Leukoc Biol 93(6):875-881 (2013).
Thierry et al., "Delivery Platform for Hydrophobic Drugs: Prodrug Approach Combined with Self-Assembled Multilayers," J. Am. Chem. Soc. 127:1626-1627 (2005) (with supporting information).
Orenstein et al., "Comparative Analysis of Histopathologic Effects of Synthetic Meshes Based on Material, Weight, and Pore Size in Mice," J Surg Res 176:423-429 (2012).
Pajarinen et al., "Innate Immune Reactions in Septic and Aseptic Osteolysis Around Hip Implants," J. Long-term Eff. Med. Implants 24(4):283-296 (2014).
Pajarinen et al., "Modulation of mouse macrophage polarization in vitro using IL-4 delivery by osmotic pumps," J. Biomed. Mater. Res. Part A 103 A:1339-1345 (2015).
Pierce et al., "Long-term histologic response to synthetic and biologic graft materials implanted in the vagina and abdomen of a rabbit model," Am J Obstet Gynecol 200:546.e1-546.e8 (2009).
Porta et al., "Molecular and epigenetic basis of macrophage polarized activation," Semin Immunol 27:237-248 (2015).
Rath et al., "Metabolism via arginase or nitric oxide synthase: two competing arginine pathways in macrophages," Front. Immunol. 5:532 (2014).
Reeves et al., "Controlled release of cytokines using silk-biomaterials for macrophage polarization," Biomaterials 73:272-283 (2015).
Sacerdote, "Opioids and the immune system," Palliat. Med. 20:s9-s15 (2006).
Sato et al., "The effect of local IL-4 delivery or CCL2 blockade on implant fixation and bone structural properties in a mouse model of wear particle induced osteolysis," J. Biomed. Mater. Res. Part A 104A:2255-2262 (2016).
Shah et al., "Adaptive growth factor delivery from a polyelectrolyte coating promotes synergistic bone tissue repair and reconstruction," PNAS USA 111(35):12847-12852 (2014).
Shah et al., "Surface-Mediated Bone Tissue Morphogenesis from Tunable Nanolayered Implant Coatings," Sci Transl Med 5:191ra183 (2013).
Shah et al., "Tunable dual growth factor delivery from polyelectrolyte multilayer films," Biomaterials 32:6183-6193 (2011).
Shukla et al., "Chitosan-based nanomaterials: a state-of-the-art review," Int J Biol Macromol 59:46-58 (2013).
Sicari et al., "The promotion of a constructive macrophage phenotype by solubilized extracellular matrix," Biomaterials 35:8605-8612 (2014).
Smith et al., "Layer-by-Layer Platform Technology for Small-Molecule Delivery," Angew. Chem. Int. Ed. 48:8974-8977 (2009).
Spiller et al., "Sequential delivery of immunomodulatory cytokines to facilitate the M1-to-M2 transition of macrophages and enhance vascularization of bone scaffolds," Biomaterials 37:194-207 (2015).
Sussman et al., "Porous Implants Modulate Healing and Induce Shifts in Local Macrophage Polarization in the Foreign Body Reaction," Ann Biomed Eng 42(7):1508-1516 (2014).
Tugal et al., "Transcriptional Control of Macrophage Polarization," Arterioscler Thromb Vasc Biol 33:1135-1144 (2013).
Udpa et al., "Effects of Chitosan Coatings on Polypropylene Mesh for Implantation in a Rat Abdominal Wall Model," Tissue Eng Part A 19(23-24):2713-2723 (2013).
Van Bilsen et al., "Ongoing foreign body reaction to subcutaneous implanted (heparin) modified Dacron in rats," J Biomed Mater Res 68A:423-427 (2004).
Wang et al. (Proc. Natl.Acad. Sci. USA. 1997(94):1657-1662); 2 pages. (Year: 1997).
Wolf et al., "Macrophage polarization in response to ECM coated polypropylene mesh," Biomaterials 35(25):6838-6849 (2014).
Wynn et al., "Macrophages in Tissue Repair, Regeneration, and Fibrosis," Immunity 44:450-462 (2016).
Wynn et al., "Origins and Hallmarks of Macrophages: Development, Homeostasis, and Disease," Nature 496(7446):445-455 (2013).
Xue et al., "Transcriptome-Based Network Analysis Reveals a Spectrum Model of Human Macrophage Activation," Immunity 40:274-288 (2014).

\* cited by examiner

- Coated (no IL-4) mesh
- IL-4 loaded mesh (20 B)
- IL-4 loaded mesh (40B)
- IL-4 loaded mesh (60B)

FIGURE 8A
FIGURE 8B
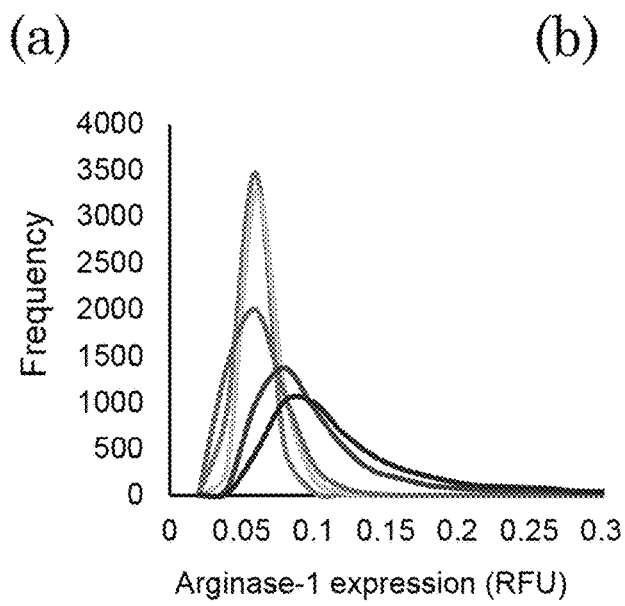
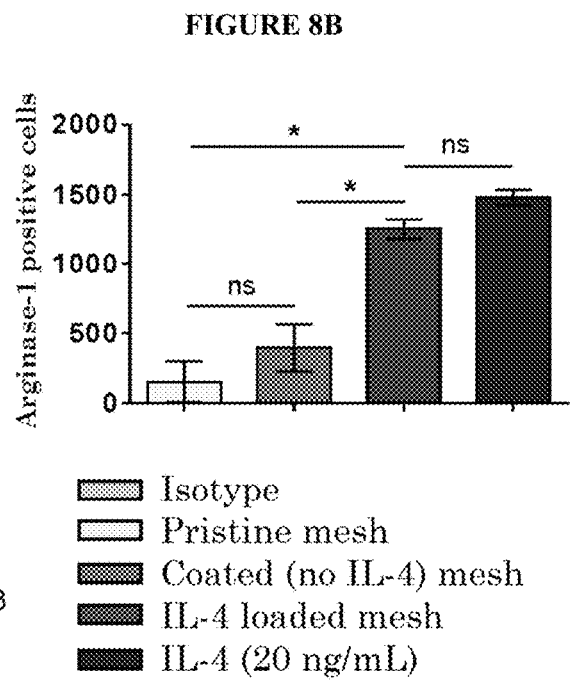

LAYER BY LAYER COATED MESH FOR LOCAL RELEASE OF BIO-ACTIVE PROTEINS

2. CROSS-REFERENCE TO RELATED APPLICATIONS

This application is a continuation of U.S. patent application Ser. No. 16/741,269, filed on Jan. 13, 2020, which is a continuation of U.S. patent application Ser. No. 15/459,993, filed on Mar. 15, 2017, now U.S. Pat. No. 10,576,187, which claims priority to U.S. Provisional Application No. 62/308,574, filed Mar. 15, 2016, the contents of which are hereby incorporated by reference herein and from which priory is claimed.

1. GRANT INFORMATION

This invention was made with government support under Grant Nos. HD043441 and GM107882 awarded by the National Institute of Health. The government has certain rights in the invention.

3. INTRODUCTION

The present invention relates to biomaterials coated with an active agent eluting coating, wherein implantation of the coated biomaterial results in modulation of the local immune reaction and reduced implant-related complications and/or improved integration of the biomaterial into the host tissue.

4. BACKGROUND OF THE INVENTION

The interaction of the host immune system with implantable materials has historically been considered to be a negative occurrence associated with downstream encapsulation and/or implant failure; however, it is now increasingly recognized that host-implant interactions can play both positive and negative roles following placement. In particular, macrophages have been described as key mediators of the host-implant interaction and critical determinants of downstream integration and functionality.

The host response to implanted materials begins immediately upon introduction of the material into the host tissue and encompasses multiple overlapping phases including injury, protein adsorption, acute inflammation, chronic inflammation, foreign body reaction, granulation tissue formation and eventual encapsulation (1). It is recognized that the early interactions which occur at the material-tissue interface represent the initiating events which drive subsequent paracrine and autocrine processes of the host response and subsequent tissue remodeling with significant implications for downstream performance. Recently, macrophage-implant interactions in particular have received considerable attention as a primary determinant of the outcome of biomaterials placement (2-7). A spectrum of macrophage phenotypes contained between two extremes has been identified, ranging from pro-inflammatory (M1) to anti-inflammatory/regulatory (M2) phenotypes, with significant implications in disease, tissue remodeling following injury, and biomaterial performance (3, 8-12). Materials which elicit improved or regenerative remodeling outcomes are associated with a shift from an initially M1 to a more M2 profile during the early stages of the inflammatory response which follows implantation (13-19). Therefore, there is a need in the art for implantable biomaterial that directly modulates the early-stage macrophage response against the biomaterial in order to promote downstream tissue integration and functional remodeling in the long-term.

5. SUMMARY OF THE INVENTION

The present invention relates to biomaterials coated with an active agent eluting coating, wherein implantation of the coated biomaterial results in modulation of the local immune reaction and reduced implant-related complications and/or improved integration of the biomaterial into the host tissue and further relates to kits containing the coated biomaterial. The present invention also relates to methods and kits for coating the biomaterial. It is based, at least in part, on the discovery that biomaterial coated with a cytokine eluting coating resulted in the shift of early stage macrophage polarization that was associated with positive long-term effects such as minimized capsule formation and improved tissue quality and composition as compared to uncoated biomaterials.

The present invention provides coated biomaterials. In certain embodiments, the biomaterials are coated with at least one polycation layer, at least one polyanion layer, and at least one active agent containing layer. In certain embodiments, the active agent is released from the coating and polarizes macrophages to an M2 phenotype. In certain embodiments, the biomaterial can be, but is not limited to, mesh, sutures, wound dressings, intraocular lenses, decellularized matrices, bone plates, joint replacements, biosensors, catheters, pacemakers, artificial organs, stents, ventricular assist devices, and neural electrodes.

In certain non-limiting embodiments, the polycation (which can be comprised of one or more species of cation) can be, but is not limited to, one or more polysaccharide (e.g., chitosan), one or more protein (e.g., collagen), a synthetic polyamine, or positively charged polymers or copolymers. In certain non-limiting embodiments, the polyanion (which can be comprised of one or more species of anion) can be, but is not limited to, glycosaminoglycan (e.g., dermatan, dermatan sulfate, hyaluronate, an alginate, chondroitin sulfate, heparan sulfate, or any combination thereof or negatively charged polymers or copolymers (e.g., polyacrylates, polyesters, polyurethanes). In certain non-limiting embodiments, the active agent can be a cytokine (e.g., IL-4, IL-13, IL-10, TGF-β, HGF or combinations thereof, or one or more glucocorticoid or combination of glucocorticoids). In certain non-limiting embodiments, the active agent is released to provide an effective concentration of the active agent locally at the tissue-implant interface, e.g., at distances of from about 10 μm to about 100 μm, or up to about 50 μm from the coated biomaterial.

In certain non-limiting embodiments, the coating on the biomaterial can have a thickness ranging from 0.5 nm to a 500 μm. In certain embodiments, the coated biomaterial comprises a total of about 10 to about 1000 of alternating polycation and polyanion bilayers. In certain non-limiting embodiments, the alternating polycation and polyanion layers do not contain an active agent. In certain non-limiting embodiments, the alternating polycation and polyanion layer coated biomaterial is coated with at least one active agent containing layer on top of the alternating polycation and polyanion layers. In certain non-limiting embodiments, the coated biomaterial comprises about 10 to about 1000 active agent containing layers. In certain non-limiting embodiments, the coated biomaterial comprises about 40 active agent containing layers on top of about 10 alternating polycation and polyanion bilayers.

The present invention provides a method for coating a biomaterial. In certain non-limiting embodiments, the biomaterial is negatively charged. In certain non-limiting embodiments, the biomaterial has a net negative or a net positive charge. In certain non-limiting embodiments, the negatively charged biomaterial is coated with a polycation layer. In certain non-limiting embodiments, the biomaterial is first treated to induce either a positive or negative surface charge to facilitate coating. In certain non-limiting embodiments, the polycation layer is coated with a polyanion layer. In certain non-limiting embodiments, the biomaterial is coated with alternating polycation and polyanion layers. In certain non-limiting embodiments, once the biomaterial is coated with alternating polycation and polyanion layers, the coated biomaterial is coated with at least one layer containing at least one active agent. In certain non-limiting embodiments, the coated biomaterial is sterilized.

6. BRIEF DESCRIPTION OF THE FIGURES

FIG. 1 illustrates a Layer by Layer coating procedure performed on polypropylene surgical meshes.

Figure 2A:
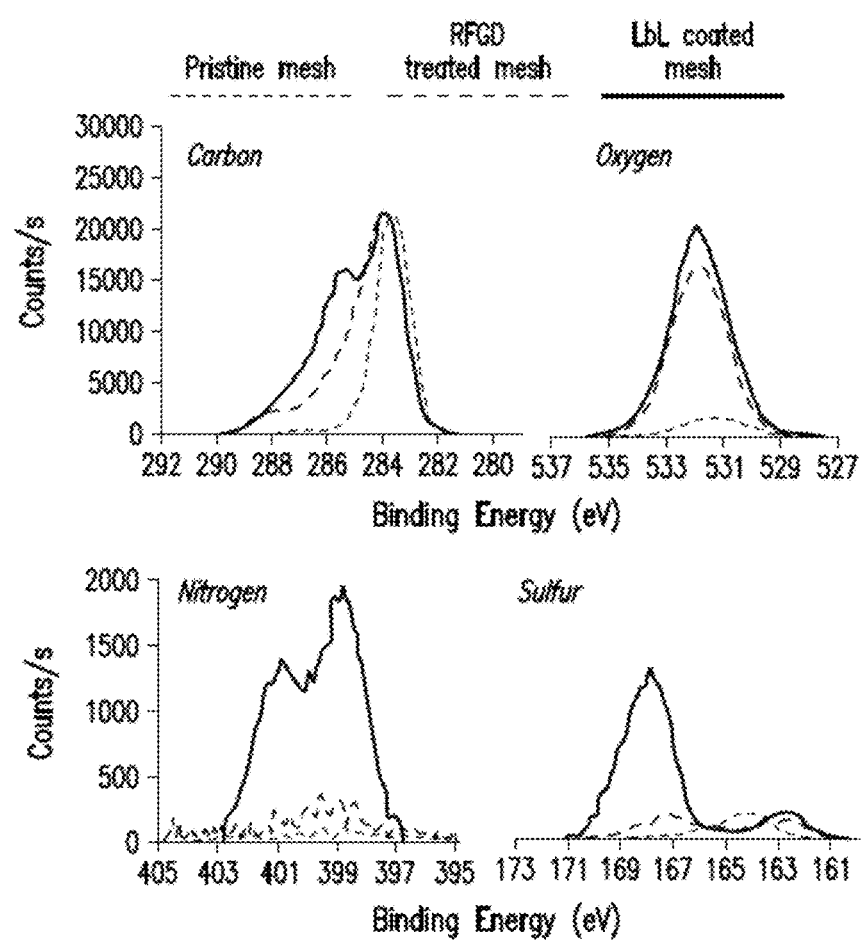

FIG. 2A provides x-ray photoelectron spectroscopy spectra (XPS) of LbL coated (dark gray), RFGD treated (gray) and pristine (light gray) mesh.

Figure 2B:
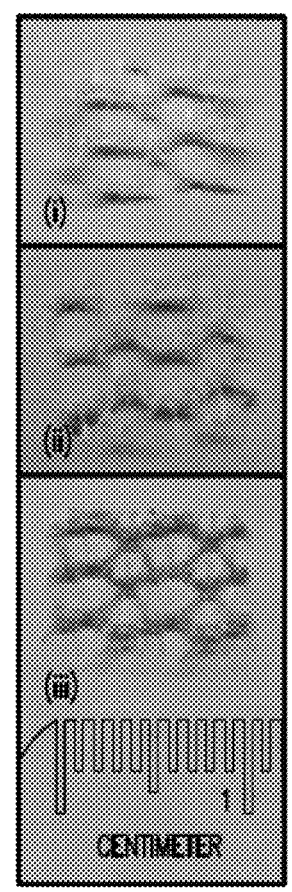

FIG. 2B provides images of alcian blue stained 1 $cm^2$ pieces of pristine (i), RFGD treated (ii) and LbL coated meshes (iii).

Figures 3A, 3B, 3C, 3D:
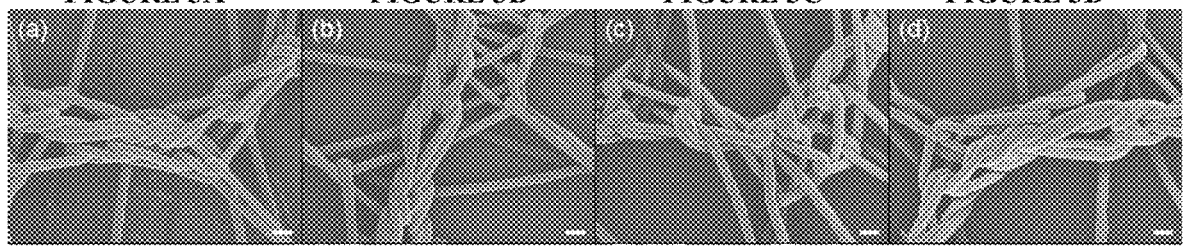
Figures 3E, 3F, 3G, 3H:
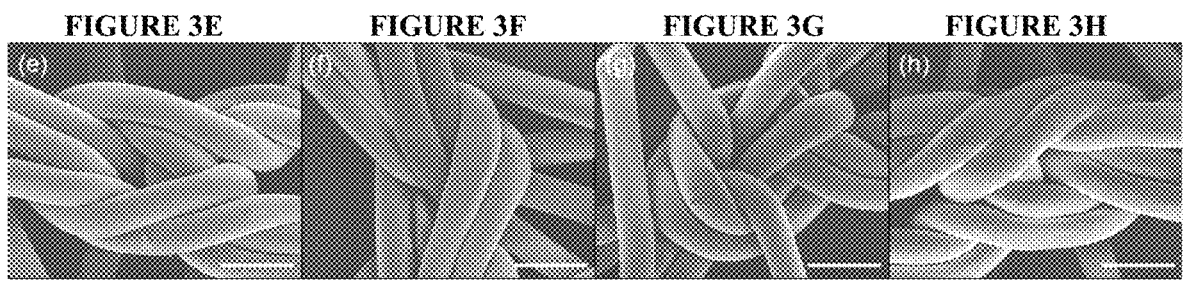

FIGS. 3A-3H provide scanning electron microscopy images of meshes, where FIGS. 3A-3D provide images at 40× FIGS. 3E-3H provide images at 150×. FIGS. 3A and 3E show pristine meshes; FIGS. 3B and 3F show RFGD treated meshes; FIGS. 3C and 3G show LbL coated meshes; and FIGS. 3D and 3H show IL-4 loaded [40B] meshes. In FIGS. 3A-3H, scale bars represent 200 µm.

Figure 4A:
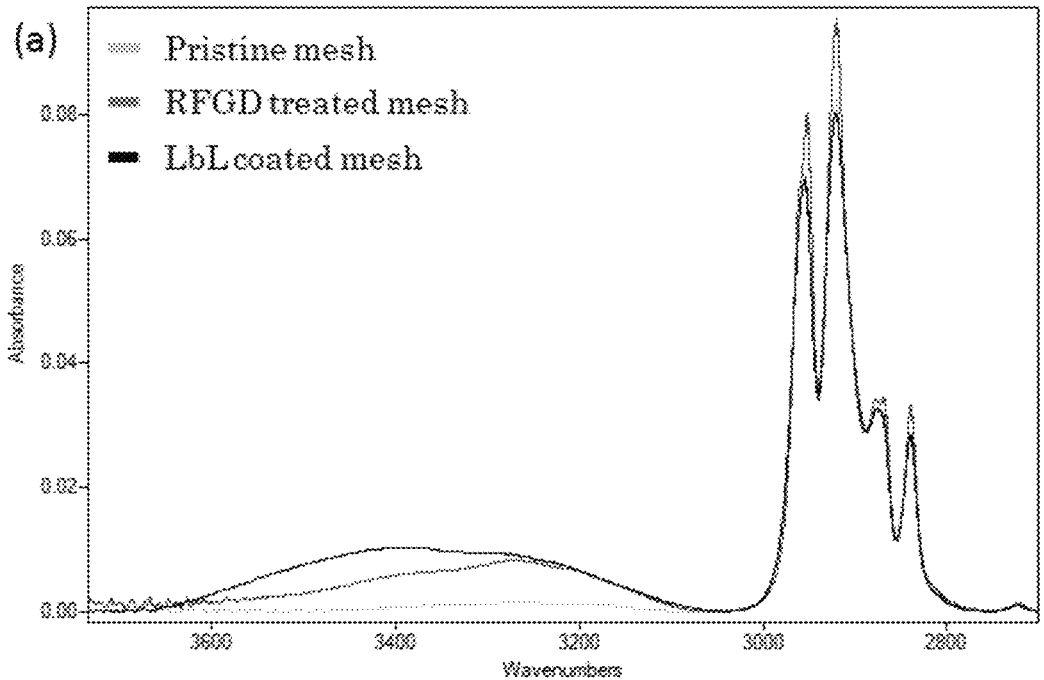
Figure 4B:
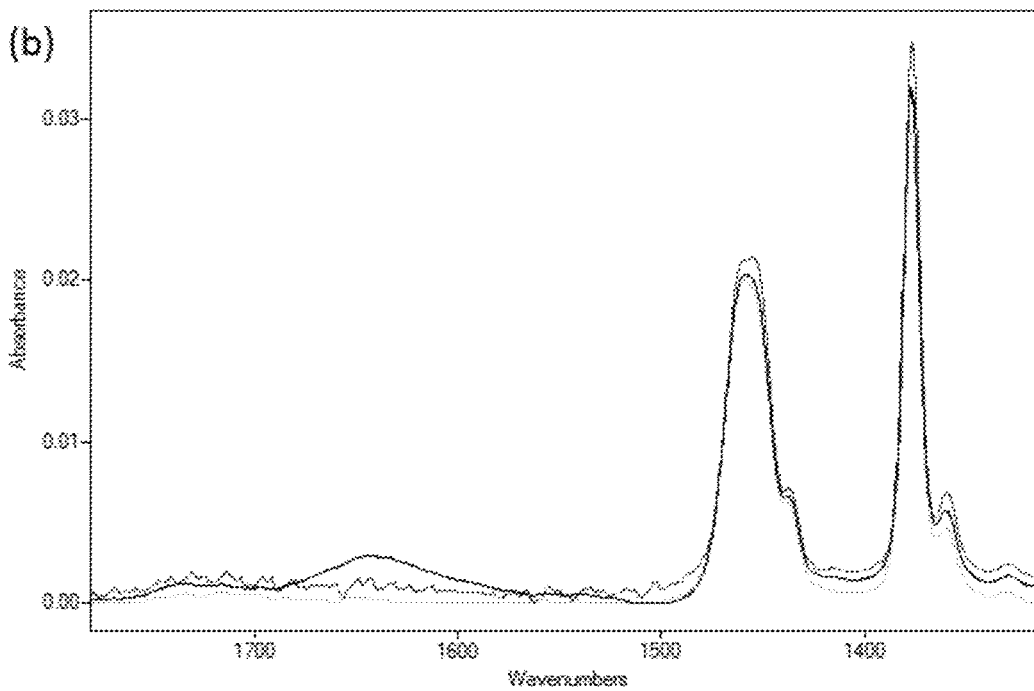

FIGS. 4A-4B provide attenuated total reflectance—Fourier transform infrared (ATR-FTIR) spectra of pristine (blue), RFGD treated (red) and LbL coated (green) meshes from wavelengths 2800-3700 $cm^{-1}$ (FIG. 4A) and 1300-1800 $cm^{-1}$ (FIG. 4B).

Figure 5A:
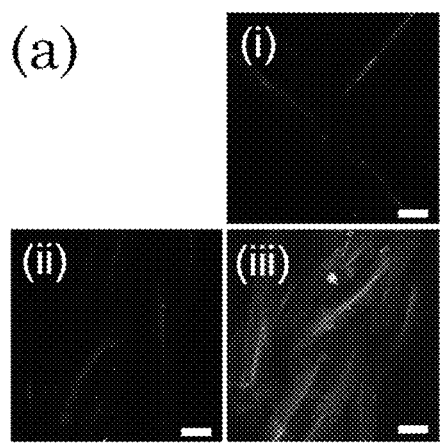

FIG. 5A provides confocal microscopy images of IL-4 immunolabeled polypropylene fibers of pristine (i), coated [no IL-4] (ii) and IL-4 loaded [40B] (iii) mesh. Scale bars represent 100 µm.

Figure 5B:
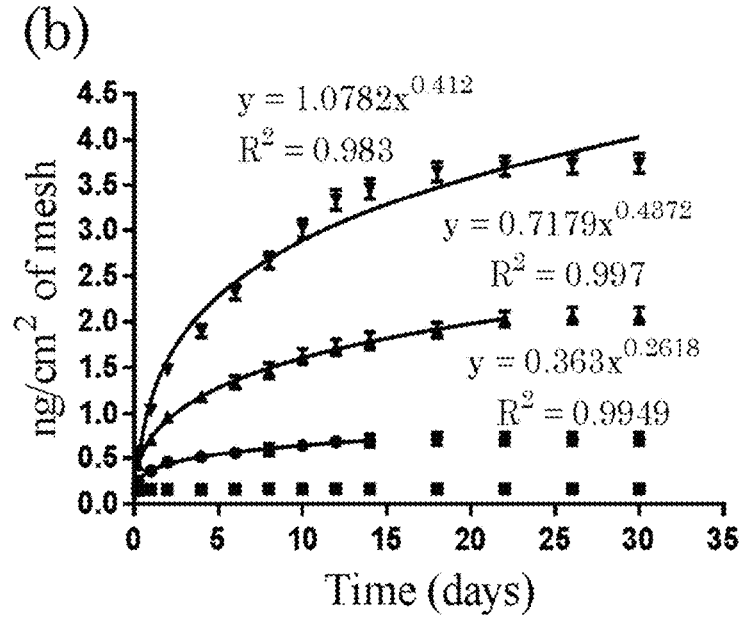

FIG. 5B provides cumulative release of IL-4 (nanograms) versus time (days) from 1 $cm^2$ pieces of IL-4 loaded mesh (20, 40 and 60 bilayers). Coated (no IL-4) mesh was used as a control. Power law dependence curves along with equations and coefficients are presented.

Figure 6:
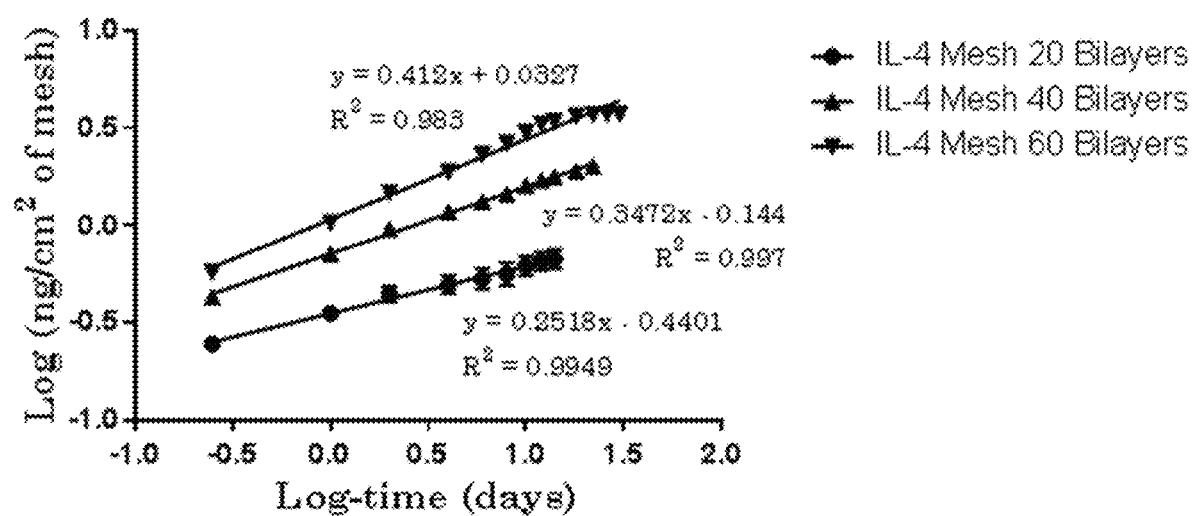

FIG. 6 shows the log-log linear fittings of IL-4 cumulative release versus time.

Figure 7A:
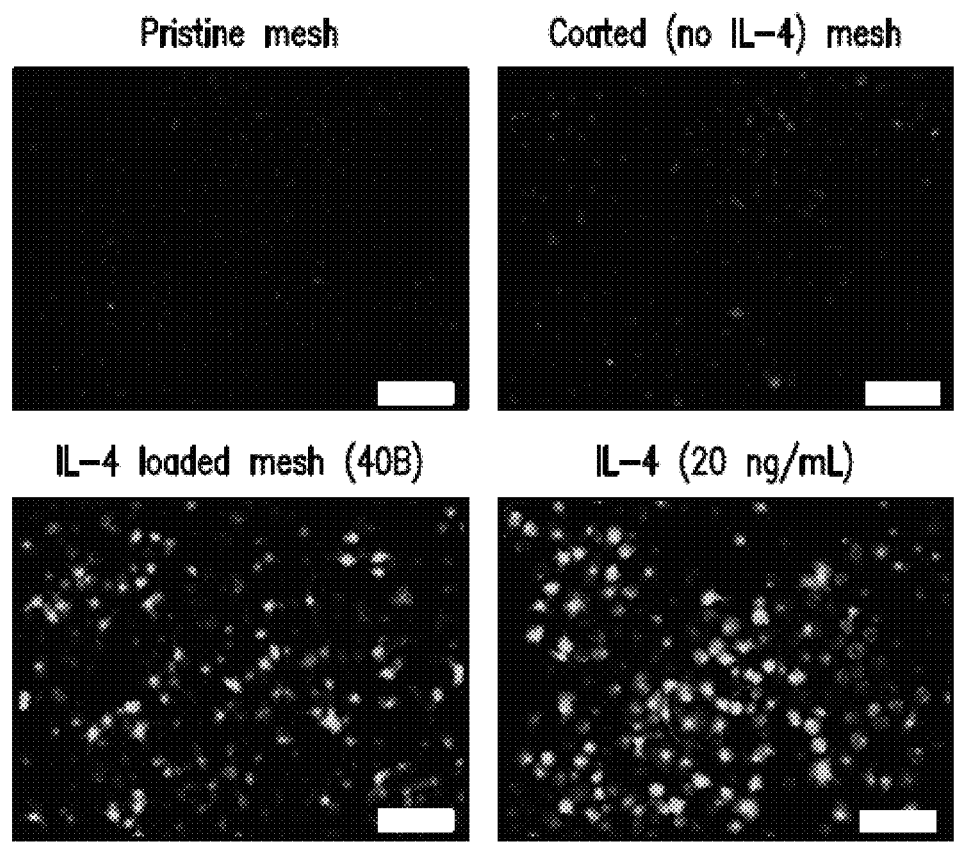

FIG. 7A illustrates arginase-1 immunolabelled bone marrow-derived macrophage cultures exposed to 1 $cm^2$ pieces of pristine, coated (no IL-4) and IL-4 loaded (40B) meshes for 72 hrs. IL-4 (20 ng/mL) was used as positive control. Scale bars represent 100 µm.

Figure 7B:
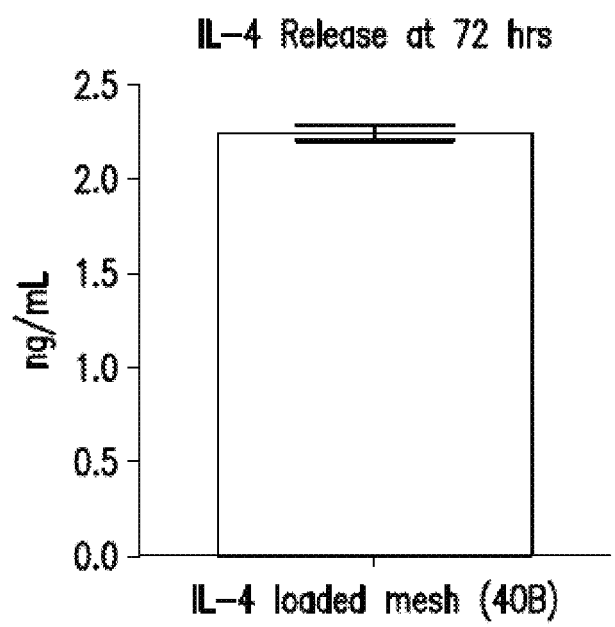

FIG. 7B shows the concentration of IL-4 released by IL-4 loaded meshes (40 bilayers) for 72 hours. Bars represent the mean±SEM.

FIG. 8A provides CellProfiler image analysis from arginase-1 immunolabeled macrophages in an in-vitro culture exposed to 1 $cm^2$ pieces of pristine, coated [no IL-4] and IL-4 loaded [40B] mesh. Isotype and IL-4 [20 ng/mL] were used as negative and positive controls, respectively.

FIG. 8B shows the number of arginase-1 positive macrophages determined from the CellProfiler analysis of FIG. 8A. Bars represent the mean±SEM. (*) Statistically significant ($p<0.05$), using one-way ANOVA and Tukey's test. (ns) Non-significant.

Figure 9:
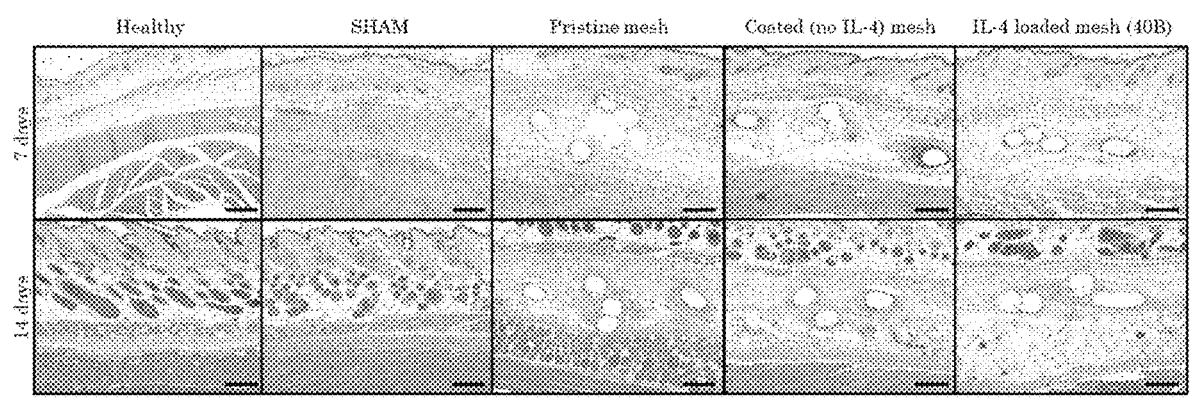

FIG. 9 shows H&E stained tissue sections at 10× from mice implanted with a 1 $cm^2$ piece of pristine, coated (no IL-4) and IL-4 loaded (40B) mesh at 7 days (top panel) and 14 days (bottom panel). Healthy and SHAM (no mesh surgery) were used as controls. Scale bars represent 200 µm.

Figure 10A:
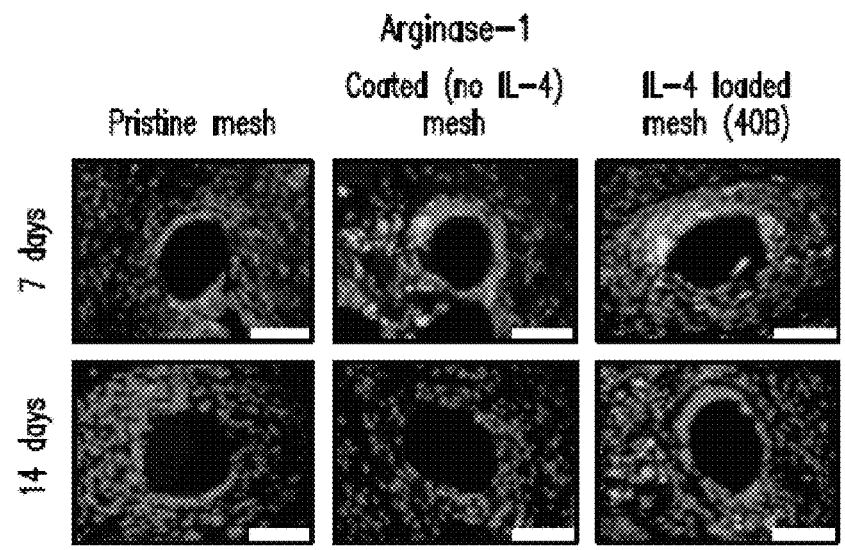

FIG. 10A shows arginase-1 immunolabeled (brighter cells) tissue sections of mice implanted with a 1 $cm^2$ piece of pristine, coated (no IL-4) and IL-4 loaded (40B) mesh for 7 days (top panel) and 14 days (bottom panel). DAPI was used to stain cell nuclei. Scale bars represent 40 µm.

Figure 10B:
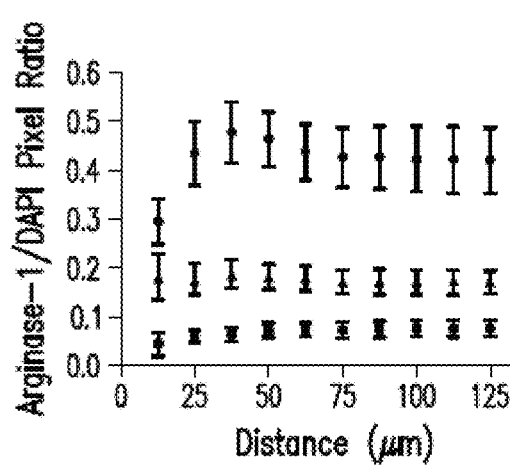

FIG. 10B illustrates the arginase-1/DAPI pixel ratio versus distance of arginase-1 immunolabeled tissue sections at 7 days.

Figure 10C:
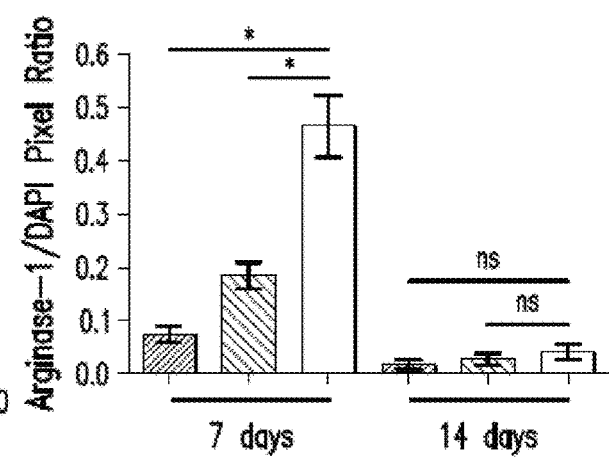

FIG. 10C provides the arginase-1/DAPI pixel ratio at 50 µm of arginase-1 immunolabeled tissue sections at 7 and 14 days. Points and bars represent the mean±SEM (N=7-9). (*) Statistically significant ($p<0.05$), using one-way ANOVA and Tukey's test. (ns) Non-significant.

Figure 10D:
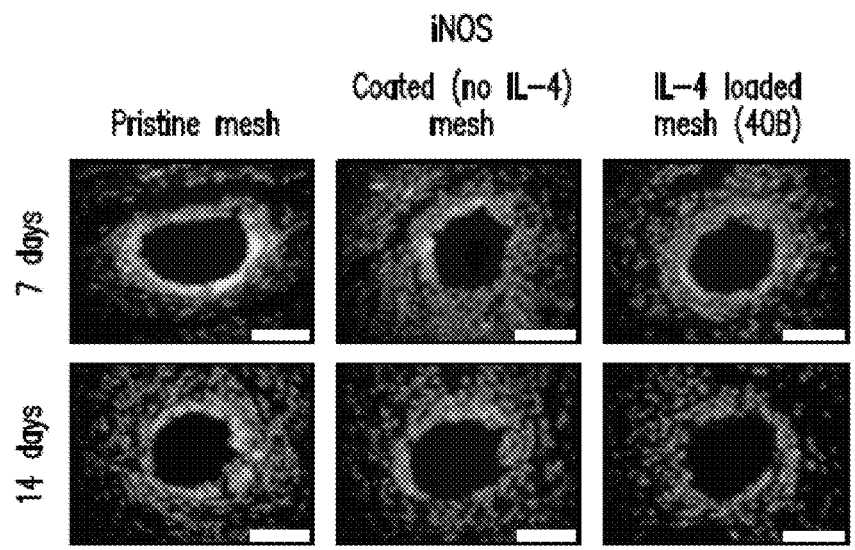

FIG. 10D shows iNOS immunolabeled (brighter cells) tissue sections of mice implanted with a 1 $cm^2$ piece of pristine, coated (no IL-4) and IL-4 loaded (40B) mesh for 7 days (top panel) and 14 days (bottom panel). DAPI was used to stain cell nuclei. Scale bars represent 40 µm.

Figure 10E:
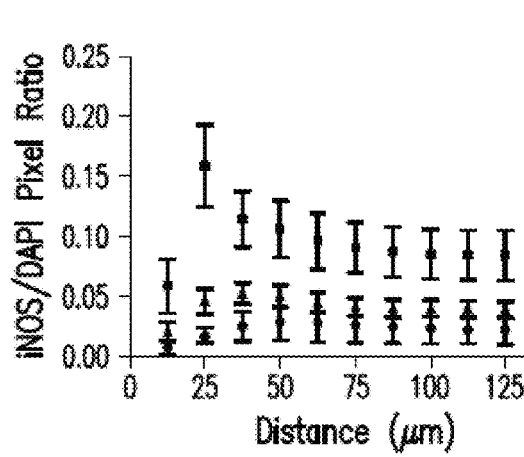

FIG. 10E illustrates the iNOS/DAPI pixel ratio versus distance of iNOS immunolabeled tissue sections at 7 days.

Figure 10F:
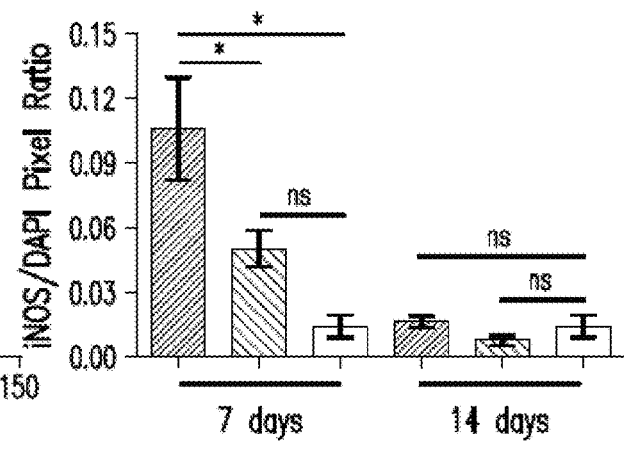

FIG. 10F provides the iNOS/DAPI pixel ratio at 50 µm of iNOS immunolabeled tissue sections at 7 and 14 days. Points and bars represent the mean±SEM (N=7-9). (*) Statistically significant ($p<0.05$), using one-way ANOVA and Tukey's test. (ns) Non-significant.

Figure 11A:
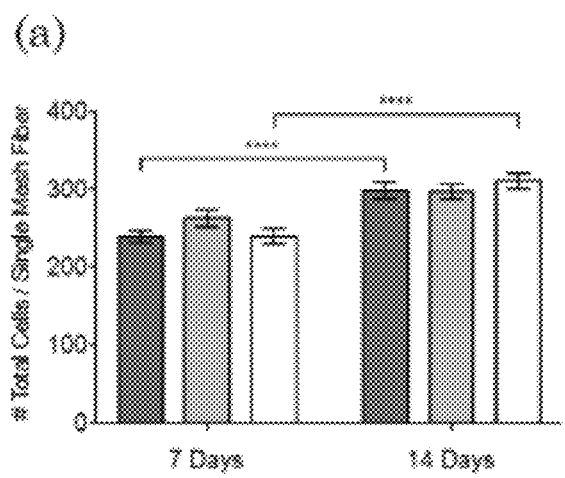
Figure 11B:
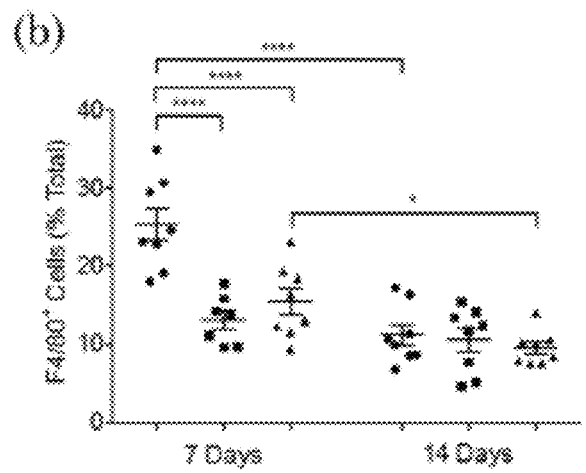
Figure 11C:
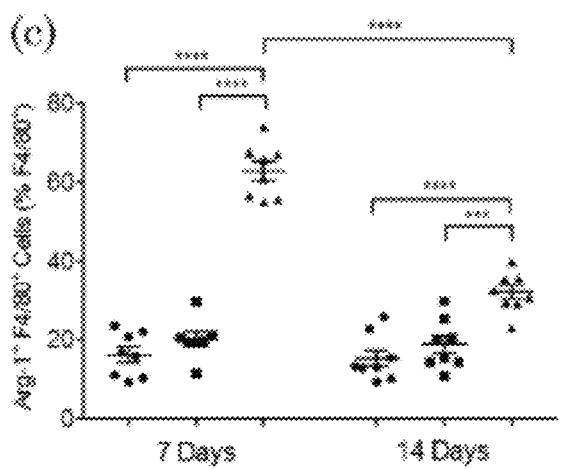
Figure 11D:
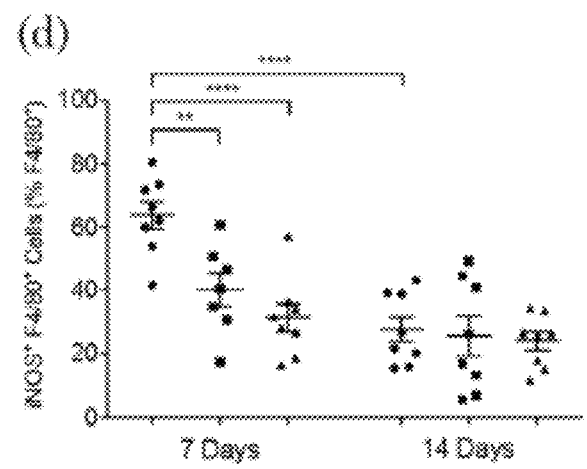

FIGS. 11A-11D provide image analysis of cells. FIG. 11A shows total cells (DAPI) and FIG. 11B shows F4/80þ cells as percentages of total cells (DAPI) surrounding single mesh fibers of tissue cross sections of mice implanted with a 1 $cm^2$ piece of pristine, coated (no IL-4) and IL-4 loaded (40B) mesh for 7 days and 14 days. FIG. 11C shows arginine-1 positive F4/80 positive cells and FIG. 11D shows iNOS positive F4/80 positive cells as percentages of total F4/80 positive cells surrounding single mesh fibers of tissue cross sections of mice implanted with a 1 $cm^2$ piece of pristine, coated (no IL-4) and IL-4 loaded (40B) mesh for 7 days and 14 days. Bars and points represent the mean±SEM (N=8). Statistical significance as (*) $p<0.05$, () $p<0.01$, (*) $p<0.001$ and (****) $p<0.0001$, using two-way ANOVA with Tukey's (groups) and Sidak's (days) tests. All other differences are non-significant.

Figure 12A:
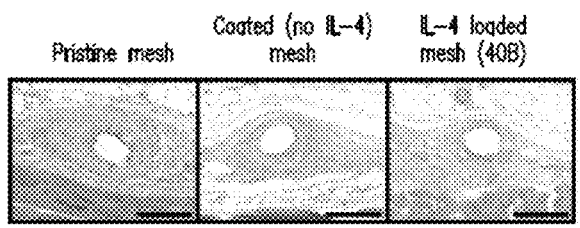

FIG. 12A shows Masson's Trichrome stained tissue sections of mice implanted with a 1 $cm^2$ piece of pristine, coated (no IL-4) and IL-4 loaded (40B) mesh at 90 days. Scale bars represent 200 µm.

Figure 12C:
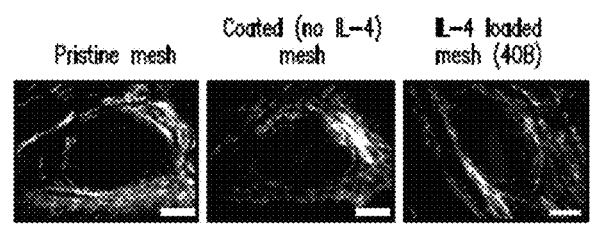
Figure 12B:
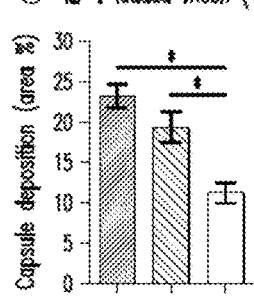

FIG. 12B provides image analysis of capsule deposition (area %) surrounding mesh fibers (3 images of a single fiber at 20× per sample, N=8 samples). Bars represent the mean±SEM. (*) Statistically significant ($p<0.05$), using two-way ANOVA and Tukey's test. All other mean differences are non-significant.

FIG. 12C shows Picro Sirius Red stained tissue sections (20×) of mice implanted with a 1 $cm^2$ piece of pristine, coated (no IL-4) and IL-4 loaded (40B) mesh at 90 days. Scale bars represent 100 µm.

Figure 12D:
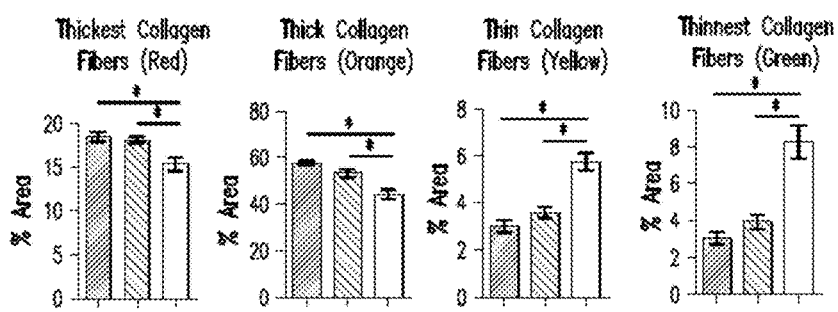

FIG. 12D provides image analysis of collagen capsule quality, surrounding mesh fibers (3 images of a single fiber at 20× per sample, N=8). Bars represent the mean±SEM. (*)

Statistically significant (p<0.05), using two-way ANOVA and Tukey's test. All other mean differences are non-significant.

Figure 13:
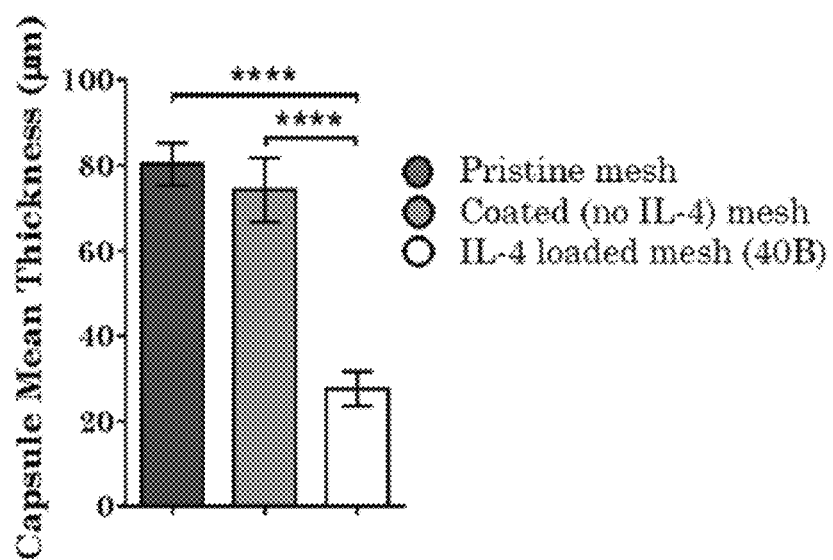

FIG. 13 provides the mean thickness surrounding mesh fibers (3 images of a single fiber at 20× per sample, N=8 samples). Bars represent the mean±SEM. Statistical significance as () p<0.01 and (**) p<0.0001, using two-way ANOVA with Tukey's test. All other differences are non-significant.

7. DETAILED DESCRIPTION OF THE INVENTION

The present invention provides biomaterials coated with an active agent eluting coating, wherein implantation of the coated biomaterial results in modulation of the local immune reaction and reduced implant-related complications and/or improved integration of the biomaterial into the host tissue and further relates to kits containing the coated biomaterial. In certain non-limiting embodiments, the biomaterials are coated with at least one polycation layer, at least one polyanion layer, and at least one active agent containing layer. In certain non-limiting embodiments, the active agent is released from the coating and polarizes macrophages to an M2 phenotype. The present invention further provides methods and kits for coating the biomaterial.

The term "biomaterial," refers to a material which has properties that are adequate for mammalian body reconstruction, medical device construction, and/or drug control/release devices or products. This term includes absorbable devices and products (e.g., absorbable sutures, absorbable clips, absorbable staples, absorbable pins, absorbable rods (for repairing broken bones), absorbable joints, absorbable vascular grafts, absorbable fabrics or meshes (e.g., for hernia repair, soft tissue patches), absorbable sponges, absorbable adhesives and absorbable drug control/release devices) as well as non-absorbable devices and products, (e.g., implantable repair or support meshes (e.g., for pelvic organ prolapse, artificial chest wall, artificial thoracic or abdominal wall prosthesis, or hernia support) acetabular or tibia components of joint prostheses, and bone cement. The term "absorbable" as used herein refers to materials that will be degraded and subsequently absorbed by the body. The term "non-absorbable" as used herein refers to materials that will not be degraded and subsequently absorbed by the body.

The terms "macrophage polarization" or "polarization of macrophages", as used interchangeably herein, refer to controlling the macrophage microenvironment to elicit a particular macrophage phenotype. Polarized macrophages can be broadly classified into two main phenotypes: 1) M1, which is pro-inflammatory and 2) M2, which is anti-inflammatory/regulatory. Materials which elicit improved or regenerative remodeling outcomes are associated with a shift from an initially M1 to a more M2 profile during the early stages of the inflammatory response which follows implantation. Macrophages can be polarized to M2 by treating the microenvironment with cytokines (e.g., IL-4, IL-13, IL-10, or combinations thereof) and/or glucocorticoids.

The term "polyelectrolyte layers" refers to coating layers that are charged. For example, the polyelectrolyte layer can be either a polycation layer or a polyanion layer. A "polyelectrolyte bilayer" refers to combination of a polycation and a polyanion polymer in a bilayer.

The term "polycation" refers to any polymer that has a net positive charge at the pH the layer is formed. Examples of polycations include, but are not limited to, a polysaccharide, a protein, a synthetic polyamine, or a synthetic polymer or polypeptide. In certain embodiments, polycation polysaccharides bearing one or more amino groups can be used herein. In certain embodiments, the polycation is the natural polysaccharide chitosan. As used herein, the term "chitosan" refers to a linear polysaccharide composed of randomly distributed 6-(1-4)-linked D-glucosamine (deacetylated unit) and N-acetyl-D-glucosamine (acetylated unit). Chitosan is produced by deacetylation of chitin. The term "chitosan" relates to chitosan, chitosan derivatives and mixtures of chitosan and chitosan derivatives (e.g., glycol-chitosan, amine-grafted chitosan, fluorescent-tagged chitosan). Similarly, the protein can be synthetic or naturally-occurring. In certain embodiments, the biodegradable polyamine is a synthetic random copolypeptide, synthetic polyamine such as poly($\beta$-aminoesters), polyester amines, poly(disulfide amines), mixed poly(ester and amide amines), and peptide crosslinked polyamines. The polycation polymers can be branched, linear, or a combination thereof.

The term "polyanion" refers to any polymer that has a net negative charge at the pH the layer is formed. Examples of polyanions include, but are not limited to, a polysaccharide, a protein, or a synthetic polymer or polypeptide. In certain embodiments, the polyanion is a polysaccharide. Examples of polyanion polysaccharides useful herein include, but are not limited to, a hyaluronate, an alginate, chondroitin sulfate, dermatan, dermatan sulfate, heparan sulfate, or any combination thereof. The polyanion polymers can be branched, linear, or a combination thereof.

The terms "tune" or "tunable", as used herein, means the ability to adjust the number and/or composition of layers of the coated biomaterial to alter the pharmacokinetic distribution of the active agent. For example, altering the number and/or composition of layers can alter active agent release characteristics such as, but not limited to, the dosage, release rates, duration, and distribution of the active agent. Tuning of the number and/or composition of layers of the coated biomaterial can be accomplished a number of ways, including but not limited to varying the number of alternating polycation and polyanion layers (e.g., increasing or decreasing the number of layers) prior to adding the active agent containing layers; varying the polycation and/or polyanion used in the alternating polycation and polyanion layers (e.g. change the polycation and/or polyanion used or utilize different combinations of polycations and/or polyanions); altering the number of active agent containing layers; altering the composition of the active agent containing layer; adding additional polycation and/or polyanion layers on top and/or in between the active agent layers.

The term "active agent" refers to an agent that is capable of having a physiological effect when administered to a subject. In certain embodiments, the term "active agent" refers to an agent that can polarize macrophages away from the M1 phenotype and/or towards the M2 phenotype for example, but not limited to cytokines (e.g., IL-4, IL-13, IL-10, or combinations thereof). and/or glucocorticoids (e.g., betamethasone, clocortolone, cortisone, dexamethasone, fludrocortisone, fluocortolone, fluprednylidene, hydrocortisone, medrysone, methylprednisolone, paramethasone, prednisolone, prednisone, prednylidene, triamcinolone, triamcinolone acetonide and their esters).

For clarity of description, and not by way of limitation, the detailed description of the invention is divided into the following subsections:
  (1) coated biomaterial;
  (2) methods of coating the biomaterial; and
  (3) kits.

7.1. Coated Biomaterials

The present invention provides biomaterials coated with an active agent eluting coating. In certain non-limited embodiments, implantation of the coated biomaterial results in modulation of the local immune reaction and reduced implant-related complications and/or improved integration of the biomaterial into the host tissue as compared to non-coated biomaterials or coated biomaterials not containing an active agent. In certain embodiments, the biomaterials are coated with at least one polycation layer, at least one polyanion layer, and at least one active agent containing layer. The number and sequence of layers can be modified in order to provide the desired amount and release time of active agent from the coated biomaterial.

In certain non-limiting embodiments, the active agent is released from the coating and polarizes macrophages away from an M1 phenotype and/or to an M2 phenotype.

In certain non-limiting embodiments, implantation of the coated biomaterial results in reduced implant-related complications as compared to non-coated or coated biomaterial not containing and active agent. For example, the coated biomaterial results in diminished formation of fibrotic capsule surrounding the implant, reduced biomaterial associated inflammation and tissue degradation, and improved tissue integration.

In certain non-limiting embodiments, implantation of the coated biomaterial results in improved integration of the biomaterial into the host tissue as compared to non-coated biomaterials or coated biomaterials not containing an active agent. For example, the coated biomaterial results in faster remodeling, faster tissue regenerations, increased functional remodeling of the tissue area, and reduced morbidities.

7.1.1. Biomaterials

The present invention provides for a coated biomaterial, wherein the biomaterial can be any material which has properties that are adequate for mammalian body reconstruction, medical device construction, and/or drug control/release devices or products as defined above. In certain non-limiting embodiments, the biomaterial can be, but is not limited to, mesh, sutures, wound dressings, intraocular lenses, decellularized matrices, bone plates, joint replacements, biosensors, catheters, pacemakers, artificial organs, stents, and ventricular assist devices. In a non-limiting embodiment, as exemplified below, the biomaterial can be a mesh for implantable repair or support (e.g., for pelvic organ prolapse, artificial chest wall, artificial thoracic or abdominal wall prosthesis, or hernia support).

The biomaterial can be made of any materials that will accept a coating. In non-limiting examples, the biomaterial can be made of polypropylene, polyesthers (e.g., Mercilene, Dacron) ePTFE, which is expanded polytetrafluoroethylene, polyurethanes, titanium, gold, and/or teflon.

In certain non-limiting embodiments, the biomaterial can be made of a material that can hold a charge and/or a net charge. The biomaterial can hold either a positive or negative charge. For example, if the biomaterial holds a negative charge, the first coating layer next to the biomaterial should be a positively charged layer, and if the biomaterial holds a positive charge, the first coating layer next to the biomaterial should be a negatively charged layer.

In certain non-limiting embodiments, the biomaterial can be, but is not limited to surgical mesh. In certain non-limiting embodiments, the mesh can be used to provide support when repairing weakened or damaged tissue. In certain non-limiting embodiments, the mesh can be used for example, but not limited to, pelvic organ prolapse. In certain non-limiting embodiments, the mesh can be a polypropylene mesh. In certain non-limiting embodiments, the mesh can be a non-absorbent polypropylene mesh (e.g., Gynemesh PS from Ethicon). In certain non-limiting embodiments, the mesh can be a canonical mesh. The mesh can be of any type, shape, size, or material.

The total number of layers of the biomaterial coating should not alter the architecture or topography of the biomaterial. For example, the biomaterial coating should not alter the biomaterial shape, size, performance, porosity, or combinations thereof.

In certain embodiments, the coating on the biomaterial can be from about 0.5 nm to about 500 µm thick. In certain embodiments, the coating on the biomaterial can be from about 1 nm to about 400 µm, about 10 nm to about 300 µm, about 20 nm to about 200 µm, about 30 nm to about 100 µm, about 40 nm to about 50 µm, about 50 nm to about 10 µm, about 60 nm to about 1 µm, about 70 nm to about 900 nm, about 80 nm to about 800 nm, about 90 nm to about 700 nm, about 100 nm to about 600 nm, about 200 nm to about 500 nm, or about 300 nm to about 400 nm thick. In certain embodiments, the coating can be from about 0.3 nm to about 0.8 nm, about 0.4 nm to about 0.7 nm, or about 0.5 nm to about 0.6 nm in thickness. In certain embodiments, the coating can be from about 1 nm to about 1000 nm, about 10 nm to about 900 nm, about 20 nm to about 800 nm, about 30 nm to about 700 nm, about 40 nm to about 600 nm, about 50 nm to about 500 nm, about 60 nm to about 400 nm about 70 nm to about 300 nm, about 80 nm to about 200 nm or about 90 nm to about 100 nm in thickness. In certain embodiments, the coating can be from about 1 µm to about 500 µm, about 10 µm to about 400 µm, about 20 µm to about 300 µm, about 30 µm to about 200 µm, about 40 µm to about 100 µm, about 50 µm, to about 90 µm, or about 60 µm to about 80 µm in thickness. In certain embodiments, the coating is no more than about 0.2 nm, about 0.3 nm, about 0.4 nm, about 0.5 nm, about 0.6 nm, about 0.7 nm, about 0.8 nm, about 0.9 nm, or about 1 nm in thickness. In certain embodiments, the coating is no more than about 2 nm, about 3 nm, about 4 nm, about 5 nm, about 6 nm, about 7 nm, about 8 nm, about 9 nm, about 10 nm, about 20 nm, about 30 nm, about 40 nm, about 50 nm, about 60 nm, about 70 nm, about 80 nm, about 90 nm, or about 100 nm in thickness.

7.1.2. Polyelectrolyte Layers

The present invention provides for a coated biomaterial, wherein the biomaterial can be coated with polyelectrolyte layers. In certain non-limiting embodiments, the biomaterial can be coated with alternating polycation and polyanion layers (i.e., polyelectrolyte bilayers) (see FIG. 1). The layer closest to the biomaterial can be either a polycation layer or a polyanion layer. The layer closest to the active agent containing layer can be either a polycation layer or a polyanion layer. In certain non-limiting embodiments, the polycation and/or polyanion layers can be distributed among and/or on top of the active agent containing layers.

In certain non-limiting embodiments, the polyelectrolytes can be antimicrobial. The polycation can be a polysaccharide, a protein, a synthetic polyamine, or a synthetic polymer or polypeptide as discussed above. The polyanion can be a polysaccharide, a protein, or a synthetic polymer or polypeptide as discussed above. In certain non-limiting embodiments, as exemplified below, the polycation is chitosan.

Chitosan has known biocompatibility, antimicrobial activity, and is degraded by activated macrophages. In certain non-limiting embodiments, as exemplified below, the polyanion is dermatan sulfate. Dermatan sulfate (also known as chondroitin sulfate B) plays a role in extracellular matrix (ECM) regulation and is able to enhance IL-4 bioactivity in-vivo. In certain non-limiting embodiments, the alternating polycation and polyanion layers can be chitosan-dermatan sulfate alternating layers. In certain embodiments, the alternating chitosan-dermatan sulfate alternating layers can provide enhanced release and bioactivity of the active agent (e.g., IL-4) in the context of macrophage mediated host-implant interactions.

The total number of alternating polycation and polyanion layers can be adjusted in order to tune the release of the active agent from the coated biomaterial. In certain embodiments, the bilayer core coating serves to make the surface charge more solid, consistent, and/or strong for the deposition of the active agent containing layers.

In certain non-limiting embodiments, the total number of alternating polycation and polyanion layers (i.e., polyelectrolyte bilayers) can be from about 10 to about 1000 bilayers. In certain embodiments, the total number of polyelectrolyte bilayers can be from about 20 to about 900, about 30 to about 800, about 40 to about 700, about 50 to about 600, about 60 to about 500, about 70 to about 400, about 80 to about 300, or about 90 to about 200. In certain embodiments, the total number of polyelectrolyte bilayers can be from about 20 to about 90, about 30 to about 80, about 40 to about 70, or about 50 to about 60. In certain embodiments, the total number of polyelectrolyte bilayers can be from about 6 to about 18 bilayers, about 8 to about 16 bilayers, or about 10 to about 14 bilayers. In certain embodiments, the total number of polyelectrolyte bilayers can be from about 8 to about 14 bilayers or about 10 to about 12 bilayers. In certain embodiments, the total number of polyelectrolyte bilayers can be at least 4 bilayers, at least 6 bilayers, at least 8 bilayers, at least 10 bilayers, at least 12 bilayers, at least 14 bilayers, at least 16 bilayers, at least 18 bilayers, or at least 20 bilayers. In certain embodiments, the total number of polyelectrolyte bilayers can be about 10 bilayers.

The polycation layer can be made of one type of polycation or a combination of different polycations. In certain embodiments, each polycation layer contains only one type of polycation. In certain non-limiting embodiments, the coated biomaterial contains more than one type of polycation, wherein the different polycations are in the same and/or different layers.

The polyanion layer can be made of one type of polyanion or a combination of different polyanions. In certain non-limiting embodiments, each polyanion layer contains only one type of polyanion. In certain non-limiting embodiments, the coated biomaterial contains more than one type of polyanion, wherein the different polyanions are in the same and/or different layers.

In certain non-limiting embodiments, the polyelectrolyte layer contains additional excipients known to those of skill in the art.

7.1.3. Active Agent Containing Layer

The present invention provides for a coated biomaterial, wherein the biomaterial can be further coated with an active agent containing layer. In certain non-limiting embodiments, the biomaterial coated with the alternating polycation and polyanion layers can be further coated with at least one active agent containing layer (see FIG. 1). The polyelectrolyte layer closest to the active agent containing layer can be either a polycation layer or a polyanion layer. In certain non-limiting embodiments, the polyelectrolyte layers can be distributed among and/or on top of the active agent containing layers.

In certain non-limiting embodiments, the active agent containing layer can include either a polycation or a polyanion. In certain embodiments, if the active agent containing layer holds a negative charge, the polyelectrolyte layer next to the active agent containing layer should be a polycation layer, and if the active agent containing layer holds a positive charge, the polyelectrolyte layer next to the active agent containing layer should be a polyanion layer.

Materials which elicit improved or regenerative remodeling outcomes are associated with a shift from an initially M1 to a more M2 profile during the early stages of the inflammatory response which follows implantation. In certain embodiments, the active agent is one that can mitigate the foreign body reaction and/or lead to improved implant integration. For example, the active agent can polarize macrophages away from the M1 phenotype and/or towards the M2 phenotype. In certain embodiments, polarization of the macrophages to the M2 phenotype will mitigate the foreign body reaction and/or lead to improved implant integration. In a non-limiting embodiment, as exemplified below, the active agent can polarize macrophages towards the M2 phenotype and away from the M1 phenotype.

The macrophage phenotype can be tested by immunocytochemistry. For example, immuno-labeling can be performed to assess the phenotypic profiles of the cells post-implantation (e.g., 7 and/or 14 days), such as testing for the presence of arginase-1 (an M2 marker) and/or inducible nitric oxide synthase (iNOS, an M1 marker). Image analysis can be performed using a custom-designed algorithm (Wolfram Mathematica, Version 10.0) in order to quantify labeling (normalized and expressed as cumulative arginase-1/DAPI pixel ratio) as a function of distance from the biomaterial surface.

The total number of active agent containing layers can be adjusted in order to tune the pharmacokinetic profile of the active agent from the coated biomaterial. In certain embodiments, the total number of active agent containing layers can be from about 10 to about 1000 bilayers. Depending on what polyelectrolyte is contained in the active agent layer, each active agent layer is separated by a polyelectrolyte layer of the opposite charge with or without an active agent. In certain embodiments, the total number of active agent containing layers can be from about 20 to about 900 layers, about 30 to about 800 layers, about 40 to about 700 layers, about 50 to about 600 layers, about 60 to about 500 layers, about 70 to about 400 layers, about 80 to about 300 layers, or about 90 to about 200 layers. In certain embodiments, the total number of active agent containing layers can be from about 20 to about 90 layers, about 30 to about 80 layers, about 40 to about 70 layers, or about 50 to about 60 layers. In certain embodiments, the total number of active agent containing layers can be from about 10 to about 75 layers, about 15 to about 60 layers, about 20 to about 55 layers, about 25 to about 50 layers, about 30 to about 45 layers or about 35 to about 40 layers. In certain embodiments, the total number of active agent containing layers can be from about 20 to about 30 layers, about 20 to about 40 layers, about 20 to about 50 layers, about 20 to about 60 layers, about 30 to about 40 layers, about 30 to about 50 layers, about 30 to about 60 layers, about 40 to about 50 layers, about 40 to about 60 layers, or about 50 to about 60 layers. In certain embodiments, the total number of active agent containing layers can be from about 22 to about 38 layers, about 24 to about 36 layers, about 26 to about 34 layers, about 28 to about 32 layers, about 32 to about 48 layers, about 34 to about 46 layers, about 36 to about 44 layers, about 38 to about 42 layers, about 42 to about 58 layers, about 44 to about 56 layers, about 46 to about 54 layers, or about 48 to about 52 layers. In certain embodiments, the total number of active agent containing layers can be at least 20 layers, at least 21 layers, at least 22 layers, at least 23 layers, at least 24 layers, at least 25 layers, at least 26 layers, at least 27 layers, at least 28 layers, at least 29 layers, at least 30 layers, at least 31 layers, at least 32 layers, at least 33 layers, at least 34 layers, at least 35 layers, at least 36 layers, at least 37 layers, at least 38 layers, at least 39 layers, at least 40 layers, at least 41 layers, at least 42 layers, at least 43 layers, at least 44 layers, at least 45 layers, at least 46 layers, at least 47 layers, at least 48 layers, at least 49 layers, at least 50 layers, at least 51 layers, at least 52 layers, at least 53 layers, at least 54 layers, at least 55 layers, at least 56 layers, at least 57 layers, at least 58 layers, at least 59 layers, or at least about 60. In certain embodiments, the total number of active agent containing layers can be about 20 layers, about 21 layers, about 22 layers, about 23 layers, about 24 layers, about 25 layers, about 26 layers, about 27 layers, about 28 layers, about 29 layers, about 30 layers, about 31 layers, about 32 layers, about 33 layers, about 34 layers, about 35 layers, about 36 layers, about 37 layers, about 38 layers, about 39 layers, about 40 layers, about 41 layers, about 42 layers, about 43 layers, about 44 layers, about 45 layers, about 46 layers, about 47 layers, about 48 layers, about 49 layers, about 50 layers, about 51 layers, about 52 layers, about 53 layers, about 54 layers, about 55 layers, about 56 layers, about 57 layers, about 58 layers, about 59 layers, about 60, about 61, about 62, about 63, about 64, about 65, about 66, about 67, about 68, about 69, about 70, about 71, about 72, about 73, about 74, about 75, about 76, about 7, about 78, about 79, or about 80.

The total number of polyelectrolyte and/or active agent containing layers can be adjusted in order to tune the release of the active agent from the coated biomaterial. For example, the composition of the layers can be altered such that the dosage, release rates, duration, and distribution of the active agent can be controlled.

In certain non-limiting embodiments, the polyelectrolyte and/or active agent containing layers can be adjusted so that the active agent is released to provide an effective concentration of the active agent at a distance of about 10 µm to about 100 µm from the coated biomaterial. In certain embodiments, the layers can be adjusted so that the active agent is released at a distance of about 15 µm to about 95 µm, about 20 µm to about 90 µm, about 25 µm to about 85 µm, about 30 µm to about 80 µm, about 35 µm to about 75 µm, about 40 µm to about 70 µm, about 45 µm to about 65 µm, or about 50 µm to about 60 µm from the coated biomaterial. In certain embodiments, the layers can be adjusted so that the active agent is released at a distance of about 5 µm to about 50 µm, about 10 µm to about 45 µm, about 15 µm to about 40 µm, about 20 µm to about 35 µm, or about 25 µm to about 30 µm. In certain embodiments, the layers can be adjusted so that the active agent is released at a distance of about 50 µm from the coated biomaterial.

In certain embodiments, the layers can be adjusted so that the active agent is released to provide an effective concentration of the active agent at a distance of up to about 100 µm, up about 95 µm, up to about 90 µm, up to about 85 µm, up to about 80 µm, up to about 75 µm, up to about 70 µm, up to about 65 µm, up to about 60 µm, up to about 55 µm, or up to about 50 µm from the coated biomaterial. As used herein, the phrase "effective concentration" means a concentration of the active agent that is able to polarize macrophages towards the M2 phenotype and away from the M1 phenotype.

In certain non-limiting embodiments, the polyelectrolyte and/or active agent containing layers can be adjusted so that the active agent is released for about 2 days to about 14 days, about 2 days to about 7 days, about 2 days to about 10 days, about 7 days to about 14 days, or about 7 days to about 10 days. In certain embodiments, the polyelectrolyte and/or active agent containing layers can be adjusted so that the active agent is released for at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In certain embodiments, the polyelectrolyte and/or active agent containing layers can be adjusted so that the active agent is released for no more than about 2 days, no more than about 3 days, no more than about 4 days, no more than about 5 days, no more than about 6 days, no more than about 7 days, no more than about 8 days, no more than about 9 days, no more than about 10 days, no more than about 11 days, no more than about 12 days, no more than about 13 days, no more than about 14 days, no more than about 15 days, no more than about 16 days, at least no more than about 17 days, at least no more than about 18 days, at least no more than about 19 days, or at least no more than about 20 days.

In certain non-limiting embodiments, the biomaterial coating provides for a delay in the release of the active agent from the coating. The delay in release can occur by coating non-active agent containing layers on top of the active agent containing layers. The number of layers can be adjusted to tune the release of the active agent from the biomaterial coating.

The active agent can be a cytokine such as IL-4, IL-13, and IL-10 or glucocorticoids such as betamethasone, clocortolone, cortisone, dexamethasone, fludrocortisone, fluocortolone, fluprednylidene, hydrocortisone, medrysone, methylprednisolone, paramethasone, prednisolone, prednisone, prednylidene, triamcinolone, triamcinolone acetonide and their esters. In certain non-limiting embodiments, as exemplified below, the active agent can be IL-4. In certain embodiments, the cytokine is complexed to the polyelectrolyte, and the concentration of the cytokine is dependent on the ratio of cytokine complexed with the polyelectrolyte and the number of active agent containing layers. For example, IL-4 can be complexed with dermatan sulfate at a particular ratio (e.g., 1.5 μg/mL IL-4 to 2 mg/mL dermatan sulfate). In certain embodiments, the ratio of active agent to dermatan can be from about 1:2000 to about 1:10. In certain embodiments, the ratio of active agent to dermatan can be from about 1:1900 to about 1:20, about 1:1800 to about 1:30, about 1:1700 to about 1:40, about 1:1600 to about 1:50, about 1:1500 to about 1:60, about 1:1400 to about 1:70, about 1:1300 to about 1:80, about 1:1200 to about 1:90, about 1:1100 to about 1:100, about 1:1000 to about 1:200, about 1:900 to about 1:300, about 1:800 to about 1:400, or about 1:700 to about 1:500.

The active agent containing layer can include one type of active agent or a combination of different active agents. In certain embodiments, each active agent containing layer contains only one type of active agent. In certain embodiments, the active agent containing layer contains more than one type of active agent, wherein the different active agents are in the same and/or different layers.

In certain non-limiting embodiments, the active agent containing layer contains additional excipients. For example, the active agent containing layer can contain a polycation and/or polyanion. In certain non-limiting embodiments, as exemplified below, the active agent can be IL-4 in combination with dermatan sulfate.

7.2. Methods of Coating the Biomaterial

The present invention also relates to methods for coating the biomaterial. In certain non-limiting embodiments, the biomaterial can be negatively or positively charged or treated such that the surface becomes negatively or positively charged. The coating process can occur by alternate cyclic deposition of multiple polyelectrolyte layers mediated by opposite electrostatic charges on the surface of a charged substrate.

In certain non-limiting embodiments, the negatively charged biomaterial can be coated with a polycation layer. In certain embodiments, the positively charged biomaterial can be coated with a polyanion layer. In certain non-limiting embodiments, the biomaterial can be coated with alternating polycation and polyanion layers. In certain non-limiting embodiments, once the biomaterial is coated with alternating polycation and polyanion layers, the coated biomaterial can be coated with at least one layer containing at least one active agent. In certain non-limiting embodiments, polycation and/or polyanion layers can be among and/or on top of the active agent containing layer(s). In certain embodiments, the coated biomaterial can be sterilized.

In certain non-limiting embodiments, the surface of the biomaterial is cleaned prior to the addition of a charge or any of the coating layers. For example, the surface of the biomaterial can be cleaned with a solution of water, acetone, isopropanol, ethanol, methanol, benzene, hydrogen peroxide, dioxane, tetrahydrofuran or combinations thereof.

In certain non-limiting embodiments, as exemplified below, the biomaterial can become charged. The biomaterial can be irradiated to form a consistent and durable charge on the surface of the biomaterial. For example, the biomaterial can be irradiated with radio frequency glow discharge (RFGD) or plasma-enhanced chemical vapor deposition (PECVD) to form either a negative or positive charge on the surface of the biomaterial.

In certain non-limiting embodiments, the polycation can be dissolved in a suitable solvent or buffer known to those of skill in the art for the particular polycation. In certain embodiments, the polyanion can be dissolved in a suitable solvent or buffer known to those of skill in the art for the particular polyanion. Suitable solvent include, but are not limited to, water and acetate, phosphate, saline buffer, acetic acid, hydrochloric acid, methanol, isopropanol, ethanol, n-propanol, n-butanol, isobutanol, t-butanol, dimethyl sulfoxide, N, N-dimethylformamide, N, N-dimethylacetamide, methyl acetate, ethyl acetate, isopropyl acetate, acetone, methyl ethyl ketone, methyl isobutyl ketone, or combinations thereof.

The biomaterial can then be soaked in a solution of the polyelectrolyte and then washed in water or buffer and allowed to dry. The coated biomaterial can then be soaked in a solution of polyelectrolyte of an opposite charge, washed in water or buffer and allowed to dry. In certain embodiments, the drying process can utilize pressurized clean air. This process can continue until the appropriate amount of layers is added to the biomaterial.

In certain non-limiting embodiments, as exemplified below, the negatively charged biomaterial can be dipped in a chitosan solution for 10 minutes at room temperature, then washed three times in milli-Q water and air dried, and once dried, the biomaterial can be dipped in a dermatan sulfate solution for 10 minutes at room temperature, then washed three times in milli-Q water and air-dried.

In certain non-limiting embodiments, once the biomaterial is coated with the appropriate amount of polyelectrolyte layers, it can be coated with an active agent containing layer. In certain embodiments, the active agent containing layer is coated on top of the biomaterial without the polyelectrolyte layers. The coated or uncoated biomaterial can be soaked in the active agent containing solution and then washed in water or buffer and allowed to dry. Depending on the polyelectrolyte present in active agent containing layer, the biomaterial is next soaked in a polyelectrolyte solution (with or without an active agent) of the opposite charge and then washed in water or buffer and allowed to dry. This process can continue until the appropriate amount of active agent containing layers are added to the biomaterial.

In certain non-limiting embodiments, as exemplified below, the biomaterial can be dipped in a solution of IL-4-dermatan sulfate mixture for 10 minutes at room temperature, then washed three times in milli-Q water and air dried, and once dried, the biomaterial can be dipped in a chitosan solution for 10 minutes at room temperature, then washed three times in milli-Q water and air-dried.

In certain non-limiting embodiments, the coated biomaterial can be sterilized using ethylene oxide gas, gamma irradiation, and E-beam sterilization.

In certain non-limiting embodiments, the method of coating the biomaterial can be as follows. For this illustration the biomaterial is a polypropylene mesh, but any biomaterial can be used. The method of coating the mesh can entail washing the biomaterial with a cleaning solution, such as, but not limited to water, acetone, isopropanol, ethanol, methanol, benzene, hydrogen peroxide, dioxane, tetrahydrofuran or combinations thereof (e.g., a 1:1 acetone:isopropanol mixture) followed by air drying. The washed mesh can then be further cleaned to, for example, remove any organic contamination by any method known by those of skill in the art. For example, the washed mesh can be irradiated with gas plasma, such as but not limited to argon plasma (e.g., at 600 W with a gas flow of 35 mL/min with a steady pressure of 250 mTorr). Once clean, the mesh can be treated to obtain a negatively charged surface. For example the cleaned mesh can be exposed to an adapted radio frequency glow discharge (RFGD) via a microwave plasma procedure (e.g., maleic anhydride can be used as a monomer for RFGD treatments followed by hydrolysis). In certain non-limiting embodiments, the mesh can be washed with water and boiled in fresh water prior to the coating process. In order to deposit a conformal coating onto the surface of negatively charged mesh, a Layer by Layer (LbL) procedure can be performed. The charged mesh can undergo alternating immersion into polycation and polyanion solutions (e.g., 2 mg/mL, 10 minutes each at room temperature) with intermediate washings in water. For example, the polycation can be chitosan (dissolved in 0.5% acetic acid for example) and the polyanion can be dermatan sulfate (dissolved in water). First, the mesh can be dipped in the polycation solution for 10 minutes at room temperature, then washed (e.g., 3 times—10, 20 and 30 seconds—in milli-Q water) and air dried (e.g., using pressurized clean air). Next, the mesh can be dipped in a polyanion solution for 10 minutes at room temperature. The mesh can then be washed again in milli-Q water and air-dried. This coating cycle can be repeated until a core coating of bilayers is achieved (e.g., 10). After coating, the mesh can be lyophilized and stored at 4° C. Next, the core coated mesh can be coated with the active agent. For example, but not by way of limitation, the active agent IL-4 (e.g., 1.5 µg/mL) can be complexed with dermatan sulfate (e.g., 2 mg/mL) by incubating the mixture overnight at 4° C. Then, the coated mesh can be further coated with 20, 40 and 60 bilayers containing the active agent using the same LbL method used for the core coating. After coating, the active agent coated loaded mesh can be lyophilized and stored at −20° C.

7.3. Kits

The present invention further provides kits that can be used to practice the invention. For example, and not by way of limitation, a kit of the present invention can comprise a coated biomaterial. In certain embodiments, a kit of the present invention can optionally comprise instructions on how to use the kit for implanting the coated biomaterial.

The present invention further provides kits for preparing the coated biomaterial. In certain embodiments, the kit of the present invention contains the polycation (in dry or liquid form) and/or polyanion (in dry or liquid form) for application on the biomaterial. When the polyelectrolyte is provided in dry form, the kit can contain the appropriate buffer or solvent to create the polyelectrolyte solution. In certain embodiments, the kits can contain the active agent and/or excipients to create the active agent containing layer. The kits can optionally contain the biomaterial to be coated and/or instructions for coating the biomaterial.

The following Example is offered to more fully illustrate the disclosure, but is not to be construed as limiting the scope thereof.

8. EXAMPLE 1: SHIFTS IN MACROPHAGE PHENOTYPE AT THE BIOMATERIAL INTERFACE VIA IL-4 ELUTING COATING

8.1. Introduction

The present example describes the development of a cytokine eluting coating for transiently shifting macrophage phenotype at the host-implant interface and demonstrates associated improvements in tissue integration of a polypropylene mesh commonly utilized in the repair of pelvic organ prolapse, a procedure associated with high rates of implant-related complications. In particular, the present example examined whether transient and controlled polarization of macrophages at the tissue-implant interface towards an anti-inflammatory/regulatory (M2) phenotype during early stages of the host response would mitigate the chronic foreign body reaction and promote better integration of polypropylene mesh into the host tissue in the long-term.

A nanometer-thick coating capable of locally releasing IL-4 (an M2 polarizing cytokine) from an implant surface (e.g., mesh in this example) in a controlled manner was developed. IL-4 was selected as it is widely used to polarize macrophages to an M2 phenotype in-vitro and a known driver of macrophage polarization in-vivo (2, 20, 21). The nanometer thickness of this coating was designed to preserve the architecture of the implantable mesh, which is commonly thought to be important for adequate tissue in growth and mechanical performance in clinical settings (22, 23). This coating is based on the layer by layer (LbL) technique (24, 25), consisting of an alternate cyclic deposition of multiple polyelectrolyte layers mediated by opposite electrostatic charges on the surface of a charged substrate (FIG. 1). This method has previously been shown to produce a tunable, uniform and conformal coating of nanometer thickness for controlled release of proteins (24-31). Therefore, the number and sequence of layers can be easily modified in order to provide the desired amount and release time of IL-4.

Results of XPS, ATR-FTIR and Alcian blue staining confirmed the presence of a uniform, conformal coating consisting of chitosan and dermatan sulfate. Immunolabeling showed uniform loading of IL-4 throughout the surface of the implant. ELISA assays revealed that the amount and release time of IL-4 from coated implants were tunable based upon the number of coating bilayers and that release followed a power law dependence profile. In-vitro macrophage culture assays showed that implants coated with IL-4 promoted polarization to an M2 phenotype, demonstrating maintenance of IL-4 bioactivity following processing and sterilization. Finally, in-vivo studies showed that mice with IL-4 coated implants had increased percentages of M2 macrophages and decreased percentages of M1 macrophages at the tissue-implant interface during early stages of the host response. These changes were correlated with diminished formation of fibrotic capsule surrounding the implant and improved tissue integration downstream. The results of this example demonstrate a versatile cytokine delivery system for shifting early-stage macrophage polarization at the tissue-implant interface and suggest that modulation of the innate immune reaction, rather than attempts to evade the immune system, may represent a preferred strategy for promoting biomaterial integration and success.

8.2. Materials and Methods

Materials

A polypropylene mesh, Gynemesh® PS (Ethicon, Somerville, N.J.) was used. Maleic anhydride, chondroitin sulfate B, chitosan (low molecular weight, deacetylation degree 85%), chondroitinase ABC, chitosanase, bovine serum albumin (BSA) and histologic staining materials were supplied by Sigma Aldrich (St. Louis, Mo.). Murine IL-4, anti-murine IL-4 antibody, murine IL-4 ELISA detection kit were supplied by Peprotech (Rocky Hill, N.J.). Mouse Arginase-1 antibody (rabbit), anti-rabbit Alexa-fluor 488 (donkey), and anti-rabbit Alexa-fluor 594 (donkey) were supplied by Abcam (Cambridge, Mass.). Mouse iNOS antibody (rabbit) was supplied by Santa Cruz (Dallas, Tex.), mouse F4/80 antibody (rat) was supplied by AbD Serotec/Bio Rad (Raleigh, N.C.), and anti-rat Alexa-fluor 488 (donkey) and anti-rabbit Alexa-fluor 546 (donkey) secondary antibodies were supplied by Thermo Fisher (Pittsburgh, Pa.).

Plasma Treatment, Layer by Layer (LbL) Coating and IL-4 Loading of Polypropylene Meshes Polypropylene (PP) meshes were cleaned using a 1:1 acetone:isopropanol mixture and then air dried prior to irradiation with 15 seconds of argon plasma at 600 W, an argon gas flow of 35 mL/min and a steady state pressure of 250 mTorr (50 mTorr initial pressure) using an Ion 40 Gas Plasma System (PVA Tepla America, Inc).

An adapted radio frequency glow discharge (RFGD) based on a previously developed microwave plasma procedure was used to obtain a negatively charged surface (32). Maleic anhydride (MA) was used as a monomer for RFGD treatments followed by hydrolysis. Alternating immersion into chitosan and dermatan sulfate solutions (2 mg/mL, 10 minutes each at room temperature) with intermediate washings in water was then performed. This cycle was repeated until desired number of bilayers was achieved. IL-4 was incubated with dermatan sulfate prior to the coating procedure for IL-4 containing mesh groups.

In particular, maleic anhydride powder (1.5 gr) was placed into a glass plate inside of the machine chamber. 1 cm$^2$ pieces of PP mesh were then placed around the plate to a distance of 8.5 cm. After an initial pressure of 50 mTorr was reached, 30 seconds of maleic anhydride plasma treatment was performed at 600 W, an argon gas flow of 35 mL/min and a steady state pressure of 250 mTorr. Finally, in order to remove the physisorbed maleic anhydride and to hydrolyze the anhydrides and produce carboxylic acid groups (negatively charged at physiological pH), PP meshes were rinsed for 30 minutes with milli-Q water and then boiled for 20 minutes in fresh milli-Q water.

In order to deposit a conformal coating of nanometric thickness onto the surface of negatively charged PP meshes, a Layer by Layer (LbL) procedure was performed. Chitosan was chosen as polycation and dermatan sulfate (chondroitin sulfate B) as polyanion. Chitosan was dissolved in 0.5% acetic acid and dermatan sulfate in milli-Q water. Both polyelectrolytes were prepared at a concentration of 2 mg/mL. First, meshes were dipped in chitosan for 10 minutes at room temperature, then meshes were washed 3 times (10, 20 and 30 seconds) in milli-Q water and air dried (pressurized clean air). Next, meshes were dipped in a dermatan sulfate solution for 10 minutes at room temperature. Meshes were washed again in milli-Q water and air-dried. This cycle was repeated until a core coating of 10 bilayers was achieved. After coating, meshes were lyophilized and stored at 4° C.

Prior to IL-4 loading onto the meshes, an IL-4 (1.5 µg/mL)-dermatan sulfate (2 mg/mL) mixture was made and incubated overnight at 4° C. in order to complex IL-4 into the polyanion. Then, polypropylene meshes with a 10-bilayer core coating were further coated with 20, 40 and 60 bilayers containing IL-4 (PP$^-$[CH/DS]$_{10}$[CH/DS$^{IL-4}$]$_x$, where x stands for the number of bilayers and DS$^{IL-4}$ stands for dermatan sulfate-bound IL-4). After coating, IL-4 loaded meshes were lyophilized and stored at −20° C. Coated (no IL-4) meshes were used as controls, using the same numbers of bilayers used for IL-4 loaded meshes. All mesh materials were then terminally sterilized using ethylene oxide.

In-Vitro and In-Vivo Studies

Coating characterization. An alcian blue staining was performed to stain the GAG components and reveal the coating. A 1% alcian blue solution was made on 3% acetic acid and adjusted to pH 2.5. Coated meshes and controls were re-hydrated in distilled water and then immersed into the alcian blue solution for 30 minutes at RT. Then meshes were washed in running tap water for 5 minutes and rinsed 5 minutes in distilled water. Images were taken using a standard optical camera.

Additionally, elemental composition of the coated meshes was performed using an X-ray photoelectron spectroscopy (XPS), using an ESCALAB 250Xi, Thermo Scientific (Pittsburgh, Pa.). To identify the elements in the coating/surface of the meshes, an initial survey of 10 scans was obtained and for detailed elemental information, spectra of 25 scans were obtained for Carbon, Oxygen, Nitrogen and Sulfur. Spectra data was analyzed using Advantage software, Thermo Scientific.

Finally, meshes were analyzed under Fourier transform infrared spectroscopy with attenuated total reflectance (ATR-FTIR) using a Bruker Vertex 70 (Billerica, Mass.) equipped with a germanium ATR crystal at a resolution of 1 cm$^{-1}$, 2 mm of aperture, 32 scans and processed by OPUS software to adjust the baseline, to smooth spectra and to remove H$_2$O and CO$_2$ peaks due to environmental noise.

IL-4 loading and release assays. Immunolabeling was used to qualitatively corroborate the loading of IL-4 into the coating. IL-4 loaded, coated (no IL-4) and pristine meshes were immersed in a 1% BSA solution to block non-specific adsorption of antibodies (1 h, RT). Washing was performed in between each step by dipping the meshes 4 times in 0.05% Tween 20. Then meshes were immersed and incubated in a solution of anti-murine IL-4 (from rabbit) as primary antibody (1:100 in 0.1% BSA, 2 hours, RT). Later on, meshes were immersed in a solution of anti-rabbit-Alexa Fluor 546 as a secondary antibody (1:100 in 0.1% BSA, 30 min, RT). Mesh fluorescence was observed under confocal microscopy (Leica DMI4000 B, Buffalo Grove, Ill.), in which an excitation/emission of 480/520 nm has been used to observe the mesh autofluorescence (green) and 561/572 nm to observe the specific fluorescence due to the loaded IL-4 (red).

Loading efficiency and release assays were performed following manufacturer instructions of Peprotech IL-4 ELISA kit. First, 1 cm$^2$ pieces of IL-4 loaded (20, 40 and 60 bilayers) and coated (no IL-4) meshes were immersed into 400 µL of a solution 0.05 units/mL chondroitinase ABC and 0.05 units/mL chitosanase in 1×PBS. Incubation was performed to multiple time points at 37° C., after which 400 µL of solution were aliquoted and stored at −80° C. until the end of the experiment. After collection, replacement with fresh solution was performed to continue the release assay. To perform the ELISA assays, 100 µL aliquots were used from each sample (N=9) at each time point.

To determine release profile kinetics; correlation and curve fitting analyses were performed using the data from cumulative release versus time, until the first time point where the release reaches a plateau, which corresponds to the total release. To corroborate power law dependence, besides direct curve fitting tests, a linear trend was corroborated using a LOG (cumulative release) versus LOG (time) curve.

In-vitro macrophage culture assay. An in-vitro macrophage culture assay was performed in order to demonstrate preservation of bioactivity of IL-4 released from the coated meshes. Bone-marrow mononuclear cells were obtained from murine bone marrow as previously described (51), then these cells were seeded in plates and differentiated to macrophages with DMEM, 10% FBS, 10% L929 supernatant, 1% HEPES, 2% MEM NEAA, 0.1% β-2-mercaptoethanol (Sigma Aldrich, St. Louis, Mo.) for 7 days. 5×10$^5$ cells were plated into 24-well plates with α-MEM, 10% FBS, 0.05 units/mL of both chondroitinase ABC and chitosanase. Macrophages were exposed to 1 cm$^2$ pieces of IL-4 (40 bilayers), coated (no IL-4) and pristine meshes. Immunolabeling isotype (rabbit IgG) and soluble IL-4 (20 ng/mL) were used as negative and positive controls, respectively. Cells were incubated at 37° C. and 5% CO$_2$ for 72 hours. After incubation, cells were fixed with 2% PFA and then blocked with 2% horse serum, 1% BSA, 0.1% triton X-100, 0.1% tween-20 for 1 hour at RT. Immunolabeling was performed using anti arginase-1 as primary antibody (1:200, overnight at 4° C.) and Alexa Fluor-488 (1:300, 1 hour at RT) as secondary. A 500 nM DAPI solution was used stain nuclei. Images were taken in an array of 3×3 images per each well using a Carl Zeiss Observer.Z1 microscope and then the intensity of arginase-1 staining was analyzed using Cell Profiler Image Analysis Software (Broad Institute, Cambridge, Mass.) using the same number of cells for all tested conditions.

In-vivo mouse mesh implantation. An implantation model using C57BL/6 female mice, 8-10 weeks old was used, following proper housing and treatment procedures approved by the Institutional Animal Care and Use Committee (IACUC) of the University of Pittsburgh and the National Institutes of Health Guide for the Care and Use of Laboratory Animals. A power analysis was performed to determine that 7 animals per group were required to maintain a statistical power of 80%.

Briefly, a midline incision was made and a subcutaneous pocket was created in the abdomen of each mouse in order to implant a 1 cm$^2$ piece of IL-4 loaded (40 bilayers), coated (no IL-4) or pristine mesh. PCL sutures were used to close the incision, then 0.5 mg/kg of Baytril and 0.2 mg/kg of Buprenex were administered for 3 days as antibiotic and analgesic, respectively. Buprenorphine (Buprenex), an opioid analgesic, has been studied and shown not to exert any effects or alterations in the immunological response. After 7, 14 or 90 days; mice were euthanized and skin/mesh/muscle complex tissues were harvested and fixed for 72 hours in neutral buffered formalin. Finally, fixed tissues were paraffin embedded and cross-sections of 7 μm were used for histological processing for H&E, Masson's Trichrome and Picro Sirius Red staining.

Histological staining. Paraffin embedded tissue cross-sections were used for H&E, Masson's trichrome and Picro Sirius Red staining. H&E and Masson's trichrome stained tissue sections were imaged on a Nikon Eclipse E600 microscope (Tokyo, Japan) at 10× and 20×, respectively. Picro Sirius Red stained tissue sections were imaged at 20× on a Nikon Eclipse TE2000-E (Tokyo, Japan), equipped with circularly polarized light.

ImageJ (version 1.48, NIH) equipped with a color deconvolution plug-in (version 1.5) was used to quantify the area of capsule surrounding mesh fibers at 90 days (3 different single fibers per sample, N=7 each group) in images taken from histological tissue sections stained with Masson's Trichrome.

A custom-designed algorithm (Mathworks MathLab, version R2015a. Natick, Mass.) was used to evaluate quantitatively the quality of the collagen capsule surrounding mesh fibers at 90 days (3 different single fibers per sample, N=7 each group) in images taken from histological tissue sections stained with Picro Sirius Red.

Immunolabeling of histological sections. Paraffin embedded tissue sections were deparaffinized and hydrated in a series of xylene/alcohol/water. Incubation was performed with proteinase K (1×) for 10 minutes to retrieve antigens. After 3 washes in water, samples were incubated at 37° C. in 50 mM of $CuSO_4$ in 10 mM $NH_4Ac$ buffer (pH=5), to reduce tissue background fluoresence. Slides were washed twice in TBST (25 mM Tris buffer+0.1% tween 20). Then, a 5% donkey serum+2% BSA+0.1% tween 20+0.1% triton X-100 solution was used as blocking agent (2 hours, RT). To immunolabel M2 macrophages, an arginase-1 (1:100) and F4/80 (1:50) primary antibodies were used (overnight at 4° C.), followed by anti-rabbit Alexa Fluor 594 (1:200) and anti-rat Alexa Fluor 488 (1:100) secondary antibodies (40 min at room temperature) in blocking buffer. To immunolabel M1 macro-phages, iNOS (1:100) and F4/80 (1:50) primary antibodies were used (overnight at 4° C.), followed by anti-rabbit Alexa Fluor 594 (1:100) and anti-rat Alexa Fluor 488 (1:100) secondary antibodies (40 min at room temperature) in blocking buffer. Vectashield with DAPI mounting media (Vector laboratories, Burlingame, Calif.) was used to stain nuclei and mount. Images of centered single fibers (3 different single fibers per sample, N=8 each group) were taken on a Nikon Eclipse E600 microscope equipped with epi-fluorescence at 40× and cell counts were analyzed using ImageJ (version 1.51a, NIH).

Image analysis algorithms were used to quantify the results obtained by imaging of histological tissue sections. First, a custom-designed algorithm (Wolfram Mathematica, version 10.0. Champaign, Ill.) was used to quantify both arginase-1 and iNOS expression at 7 and 14 days by means of arginase-1/DAPI and iNOS/DAPI pixel ratio versus the distance from the surface of single centered mesh fiber (3 different single fibers, N=8 each group) images taken from histological tissue sections per sample. Next image analysis was performed using ImageJ (version 1.51a, NIH) in order to quantify the number of pro-inflammatory (iNOS, M1) and regulatory (arginase-1, M2) macrophages (F4/80) surrounding single mesh fibers in each group.

Statistical Analysis

Comparisons of means were performed by either one-way or two-way analysis of variance (ANOVA), using $p<0.05$ as statistical significance criteria (one-tailed) followed by Tukey's test. Shapiro-Wilk was used to test normality. All statistical tests were performed on GraphPad Prism V6 (La Jolla Calif., USA).

8.3. Results

Surgical Mesh Plasma Irradiation, LbL Coating and Characterization

An adapted radio frequency glow discharge (RFGD) method (32) was used to form a consistent and durable negative charge on the surface of polypropylene (PP) mesh in order to facilitate the desired LbL coating. The presence of a negatively charged surface was confirmed by the appearance of two peaks at 284 eV (C—C) and 288 eV (O—C═O) on the carbon spectrum and a peak at 532 eV on the oxygen spectrum, while pristine mesh only had a peak at 284 eV (C—C) when evaluated by X-ray photoelectron spectroscopy (XPS) (FIG. 2A). RFGD treated meshes were then LbL coated using chitosan as a polycation and dermatan sulfate as a polyanion. Chitosan was chosen for its known biocompatibility, antimicrobial activity, and as activated macrophages highly express chitinase-like proteins (chitin and chitosan degrading enzymes) (33-35). Dermatan sulfate (also known as chondroitin sulfate B) was chosen for its key role in extracellular matrix (ECM) regulation and its described ability to enhance IL-4 bioactivity in-vivo (36). As such, the chitosan-dermatan sulfate LbL complex was chosen to provide enhanced release and bioactivity of IL-4 in the context of macrophage mediated host-implant interactions.

A coating of 10 bilayers was performed as core coating prior to IL-4 loading. Alcian blue staining was used to visualize the chitosan and dermatan sulfate components of the coating. Blue coloration and absence of precipitates along the mesh surface suggested the presence of a conformal and uniform coating on LbL coated meshes (FIG. 2B). Electron microscopy (FIG. 3) was used to confirm the conformal nature of the coating and showed no apparent changes in surface topography, porosity and thickness between LbL coated, RFGD treated and pristine meshes. The presence of chitosan in the LbL coating was corroborated by the appearance of two peaks at 399 eV (C—N) and 401 eV (O—C—N) in the nitrogen spectrum and the presence of dermatan sulfate by the appearance of a peak at 168 eV (C—S—O) in the sulfur spectrum when evaluated by XPS (FIG. 2A), in addition to the presence of peaks at 288 eV (O—C=O) and 286 eV (C—O) in the carbon spectrum, confirming the presence of both polyelectrolyte chains. These measurements were performed at different points on the surface of the PP mesh and spectra were identical throughout the mesh surface. These findings were consistent with ATR-FTIR measurements (FIG. 4).

IL-4 Loading, Release and Bioactivity Assessments

Mesh coated with a 10-bilayer core coating was then coated with 20, 40 and 60 additional bilayers containing IL-4. IL-4 was pre-incubated with dermatan sulfate prior to LbL coating, promoting the loading of the cytokine due to the high affinity of IL-4 (net positive charge, given its isoelectric point of 9.17) for sulfated glycosaminoglycans (negatively charged). Confocal microscopy demonstrated positive IL-4 labeling distributed throughout the entire surface of IL-4 loaded meshes in contrast to the absence of positive labeling on coated (no-IL-4) mesh and pristine mesh (FIG. 5A). ELISA assays were performed to quantify IL-4 release over time. Results showed that both the amount of IL-4 and the length of release are dependent on the number of bilayers containing IL-4 in the LbL coating (FIG. 5B). In particular, the in-vitro release of IL-4 was observed up to 14, 22 and 30 days for coatings of 20, 40 and 60 bilayers, respectively. The release profile for all IL-4 loaded meshes followed a power law dependence, regardless of the number of coating bilayers (FIG. 6). These findings are consistent with other studies done on LbL films as a platform to study protein release. Based upon these results, meshes coated with 40 bilayers containing IL-4 were selected for further in-vitro and in-vivo assays, given the desire to release IL-4 and polarize macrophages towards an M2 phenotype only at early stages of the host response, since the coating released about 90% of IL-4 only at early stages of the host response (up to 14 days). All further assays included coated (40 additional bilayers with no IL-4) and pristine mesh groups as control groups.

In order to show that IL-4 bioactivity remained after the coating procedure and terminal sterilization (by ethylene oxide), an in-vitro macrophage polarization assay was performed using bone marrow-derived macrophages. Macrophages exposed to IL-4 loaded meshes for 72 hours were fixed and immunolabelled against arginase-1, an M2 macrophage specific marker. Image analysis (CellProfiler, Broad Institute, Cambridge, Mass.) of arginase-1 positive cells (FIG. 7A) revealed that the IL-4 released from the IL-4 loaded mesh remained bioactive and able to polarize macrophages towards an M2 phenotype (FIG. 8). No significant increase of arginase-1 was observed for coated mesh compared to pristine mesh. Of note, the pattern of arginase-1 expression following exposure to IL-4 coated meshes was similar to the IL-4 positive control (20 ng/mL) despite the lower levels of IL-4 (2.25 ng/mL) released from the mesh surface at 72 h (FIG. 7B), suggesting that the coating components may enhance IL-4 bioactivity or that IL-4 is protected by the coating and released gradually.

Studies on Macrophage Polarization and the Early-Stage Host Response Against Implanted Mesh A mouse implantation model was used to test the ability of IL-4 loaded mesh to promote an early shift (7 and 14 days) in the polarization of macrophages towards an M2 phenotype in-vivo and to examine the effects of such shifts in macrophage polarization upon downstream tissue remodeling (90 days). 1 $cm^2$ of IL-4 loaded mesh (40B), coated mesh (no IL-4), or pristine mesh were implanted into a subcutaneous pocket in the abdomen of 8-10 week old female C57BL/6J mice. Mesh and surrounding tissue (muscle and skin) were then harvested at 7 and 14 days post-implantation and used to study macrophage polarization. Sham surgeries (no mesh implantation) were also performed. In sham animals, a normal wound healing process observed (FIG. 9, top panel) and was characterized by a transient inflammatory response including significant immune cell infiltration at 7 days which was largely resolved by 14 days post-inflammation with restoration of normal tissue architecture resembling healthy tissue controls. The histologic appearance in mice implanted with mesh was also characterized by the presence of inflammatory cell infiltration in the surgical site at 7 days; however, this reaction was not resolved at 14 days and was largely localized to the area surrounding mesh fibers, regardless of mesh type (FIG. 9, bottom panel), thereafter. The presence of foreign body giant cells was noted beginning at 14 days post implantation and at the 90 day time point, regardless of mesh type. While the number and distribution of foreign body giant cells was qualitatively similar across all groups, no attempt was made in the present study to quantify the number of foreign body giant cells.

Immunolabeling of F4/80 (pan macrophage marker), arginase-1 (an M2 marker) and inducible nitric oxide synthase (iNOS, an M1 marker) was performed to assess the number, location, and phenotypic profiles of the macrophages within the site of implantation at 7 and 14 days post-implantation. Image analysis was performed using a custom-designed algorithm (Wolfram Mathematica, Version 10.0) in order to quantify labeling (normalized and expressed as cumulative arginase-1/DAPI pixel ratio) as a function of distance from the mesh surface (FIG. 10). In all mesh groups, the number of both arginase-1 and iNOS positive cells were observed to peak within the first 50 μm from the mesh surface (FIGS. 10B and 10D). Therefore, this distance was considered as the tissue-biomaterial interface, where the most important interactions of the biomaterial with the surrounding tissue occur and determine the implant success in the long term.

Total cell infiltration around single mesh fibers was assessed by DAPI staining, revealing no differences between groups at 7 or 14 days (FIG. 11A). However, the small increases in the number of cells within the remodeling site were observed from 7 to 14 days in the pristine and IL-4 loaded mesh implantation groups. Analysis of F4/80 positive macrophage populations revealed a significantly higher presence of F4/80 positive cells as a percentage of the total cell population in mice implanted with pristine mesh, compared to both coated (no IL-4) and IL-4 loaded mesh groups at 7 days (FIG. 11B). At 14 days, the percentage of F4/80 positive cells in the pristine mesh group was significantly reduced and was similar to levels similar to those found in both coated (no IL-4) and IL-4 loaded meshes. The percentage of F4/80 positive cells in the implantation site of IL-4 loaded meshes were also significantly decreased compared to 7 days, but these decreases were smaller than those observed for the pristine mesh group. There were no differences in the percentage of F4/80 positive cells between coated (no IL-4) and IL-4 loaded mesh groups at 7 or 14 days. These results suggest that the coating may have had an inhibitory effect upon the recruitment of macrophages into the implantation site at early time points.

Additional co-labeling was performed for arginase-1 and iNOS to assess the M1/M2 polarization profile of the cells within the implantation site. Results at 7 days post-implantation revealed that mice implanted with IL-4 loaded mesh had an increase in the percentage of arginase-1 positive macrophages (F4/80$^+$) near the mesh surface as compared to coated mesh and pristine mesh groups (FIG. 11C). The number of arginase-1 positive cells in the IL-4 loaded mesh group was significantly increased in the first 40 to 50 µm from the mesh surface (FIGS. 10B and 10C) as compared to both coated and pristine mesh, suggesting that the effects of IL-4 released from the LbL coating are limited to distances up to 50 µm from the surface of the implanted mesh. Coated mesh did not elicit a significant increase in arginase-1 positive macrophages as compared to pristine mesh (FIG. 11C). These results are consistent with the in-vitro findings showing significant increases in M2 macrophage polarization only in the IL-4 loaded mesh group. Similarly, results at 7 days post-implantation also showed a reduction of iNOS positive cells in mice implanted with IL-4 loaded meshes compared to mice implanted with pristine meshes (FIG. 11D). Mice implanted with coated mesh also showed a reduction in iNOS positive macrophages compared to the pristine mesh implanted group; however, no significant differences were observed between the coated mesh and IL-4 loaded groups (FIG. 8D). These results suggest that the coating material may have impacted the polarization of macro-phages towards an M1 profile. Differences in iNOS labeling were observed to peak at 25 µm from the mesh surface of the pristine mesh implanted group at 7 days (FIG. 10E), again suggesting that the effects of the coating were limited to the first 50 µm from the mesh surface.

Results at 14 days post-implantation revealed a decrease in both arginase-1 and iNOS labeling as compared to 7 days, with no significant differences observed between any groups. However, the percentage of arginase-1 positive macro-phages was still higher than both coated (no IL-4) and pristine mesh groups (FIG. 11C). The percentage of iNOSA positive macrophages at 14 days was found to decline in mice implanted with pristine mesh as compared to 7 days; however, there were no significant differences observed between any groups at the 14 day time point (FIG. 11D). When the effects of IL-4 coating upon arginase-1 expression at 7 and 14 days were compared (FIGS. 10C, 10F, 11D) it can be appreciated that arginase-1 expression in the IL-4 coated group at 14 days returned to levels similar to those observed for pristine meshes at both 7 and 14 days. This suggests that the length of IL-4 release from the LbL coated meshes occurs at the early stages of the host response (<14 days), and that its effects on macrophage polarization in-vivo are declining by 14 days. Expression of iNOS in the IL-4 loaded mesh group remained low with no changes between 7 and 14 days.

While increases in the M2 macrophage population can likely be attributed to the release of IL-4 from loaded mesh as demonstrated in-vitro, there are two possible mechanisms that could explain the observed reduction in the number of iNOS positive cells in the IL-4 loaded mesh group. First, iNOS expression may be reduced as a consequence of the polarization of the macrophages at the tissue implant interface towards an M2 phenotype, given the known competitive nature of pathways leading to iNOS and arginase-1 expression in mice (37-39). Second, decreased iNOS expression may be due to effects of the coating components upon macrophage polarization, and hence a diminished M1 macrophage response. This second mechanism is supported by the significant reduction in iNOS positive macrophages (FIG. 11D) and also the reduction in F4/80$^+$ cells (FIG. 11B) observed in the coated mesh group at 7 days, compared to the pristine mesh group (FIG. 10F). Therefore, the coating components and/or the modified mesh surfaces themselves appear to have effects in the reduction of M1 macrophages but not in promoting M2 macrophage polarization. Thus, the observed results are likely a combination of mechanisms driving the reduction of M1 macrophages by IL-4 loaded meshes with IL-4 mediated increases in the M2 population.

It was noted that some arginine-1 positive and iNOS positive cells did not express F4/80. This suggests that cells other than macrophages may produce arginine-1 and iNOS in the area of implantation, or that a population of macrophages that express other markers such as CD11 b or CD68, but not F4/80, are present within the remodeling site.

Downstream Effects in the Host Response Upon Macrophage Polarization Promoted by Implanted Meshes Finally, mesh and the surrounding tissue complex were harvested at 90 days post-implantation to evaluate the effects of mesh coating and IL-4 loading upon long-term tissue remodeling outcomes. Image analysis of Masson's trichrome stained histological sections was performed to identify and quantify capsule formation. Results revealed capsule formation around mesh fibers for all groups (FIG. 12A); however, IL-4 loaded mesh elicited reduced capsule density compared to the prominent and dense capsules surrounding fibers of both coated and pristine meshes (FIGS. 12B and 13). Subsequent analysis of collagen fiber distribution in picrosirius red stained sections was performed using a custom-designed algorithm (Mathworks MatLab R2015a) to assess the quality of the collagen fibers composing the fibrotic capsule. Circularly polarized light microscopy was able to reveal the relative thickness of the collagen fibers as a function of the color hue from thin green fibers to increasingly thick yellow, orange and red fibers (40). Results revealed that mice implanted with IL-4 loaded meshes had reduced content of both thick orange and thicker red collagen fibers, compared to both pristine and coated meshes (FIGS. 12C and 12D). A concurrent increase in thin yellow and thinner green collagen fibers was found for IL-4 loaded mesh compared to both pristine and coated mesh (FIGS. 12C and 12D). These outcomes indicate a change in the quantity and type of the collagen fibers composing the fibrotic capsule and may be particularly relevant for an improved mechanical performance of the implanted mesh in-vivo.

8.4. Discussion

The results of this example demonstrate that the effects of the released IL-4 from LbL coated mesh caused a shift in early-stage macrophage polarization that was associated with positive long-term effects such as minimized capsule formation and/or improved tissue quality and composition as compared to coated and pristine meshes. These results also suggest that long-term positive outcomes are due to an increase in the proportion of M2 macrophages, rather than a decrease in the presence of M1 macrophages, given that coated meshes were capable of significantly decreasing the proportion of M1 macrophages (FIG. 10) as compared with pristine mesh, but were not associated with improved tissue remodeling outcomes (FIGS. 12A-12D). The present study demonstrated that it is possible to transiently shift the early phases of the host response to implants which otherwise elicit a chronic pro-inflammatory response with impact upon the tissue remodeling outcome downstream while leaving key implant characteristics such as material properties and porosity intact.

It has been previously suggested that excessive long-term polarization towards either an M1 or an M2 phenotypes may have negative effects on remodeling outcomes (3, 13, 41). Additionally, studies have described pathologies associated with an imbalance and long-term presence of M1 or M2 macrophages, including but not limited to cancer, diabetes and atherosclerosis (12, 42, 43). Therefore, localized and temporal delivery of bioactive agents represents an advantage over strategies promoting systemic and or permanent shifts in the host response as it limits the potential for adverse long-term interactions and exacerbation of conditions which may exist at distant sites. Similarly, promoting transient shifts in macrophage polarization in the early host response represents an improved approach as compared to strategies which seek to evade the host immune response. Previous studies using surface modification of biomaterials and coatings to escape the innate immune system have shown only modest improvements at early stages of the host response against biomaterials and few improvements in long-term performance (44-48). Finally, the present delivery system represents an advantage over previous delivery approaches, given that significant effects on macrophage polarization are observed at lower, controllable and safer doses (picograms to nanograms), compared to the high doses (nanograms to micrograms) of IL-4 used in previous studies. The systemic release of larger amounts IL-4 may lead to effects upon distal tissues and/or exacerbated and contradictory outcomes associated with a fibrotic process or potential enhancement of the foreign body reaction.

In-vivo, both the chitosan and dermatan sulfate components of the coating are degraded by macrophages and other cells participating in the host response. Layer by layer films have shown multiple release mechanisms, depending the nature of the polyelectrolytes composing the films, surface degradation being the most predominant mechanism that gradually releases the entrapped bioactive agents by degradation of the most external layer films, followed by more internal layers. Therefore, IL-4 can be released by gradual surface degradation of the coating multilayers, mainly triggered by macrophages and other cells of the immune system with enzymatic capacity. However, release by diffusion of IL-4 can also occur to a lesser extent.

In sum, the presence of a uniform and conformal coating composed of both chitosan and dermatan sulfate was demonstrated. This coating can be loaded with IL-4 in a uniform manner through the entire surface of the mesh, and the amount and length of release can be tuned by simply changing the number and sequence of coating bilayers. The released IL-4 from LbL coated meshes is bioactive and can promote macrophage polarization towards an M2 phenotype both in-vitro and in-vivo. In addition, the effects of the local released IL-4 from LbL coated meshes on macrophage polarization extend up to 50 μm of distance from the mesh surface at early stages of the host response against biomaterials. Consequently, these effects also led IL-4 loaded meshes to reduce the percentage of M1 macrophages in-vivo, compared to pristine meshes. At long term, a decreased fibrotic capsule formation surrounding mesh fibers and an improved quality of collagen fibers composing the capsule observed only in mice implanted with IL-4 loaded meshes indicates an improved resolution of the foreign body reaction. These positive long-term outcomes are mostly attributed to an increased proportion of M2 macrophages rather than a reduced presence of M1 macrophages.

Finally, these results support our hypothesis that early-stage macrophage polarization at the tissue-implant interface towards an M2 phenotype would mitigate the foreign body reaction and hence promote better integration of the mesh into the host tissue in the long term, compared to the outcomes observed from the passive and non-controlled effects on macrophage polarization promoted by different biomaterials. This example also demonstrated that strategies which include modulation of the macrophage response are beneficial for tissue integration and functional remodeling of implanted biomaterials, rather than strategies which simply seek to avoid the innate immune system. While the present study focused only upon polypropylene mesh commonly used for soft tissue reconstruction, the methods and findings presented can be extended to include other material types and applications.

9. REFERENCES

1. Anderson J M, Rodriguez A, & Chang D T (2008) Foreign body reaction to biomaterials. Semin Immunol 20(2):86-100.
2. Brown B N & Badylak S F (2013) Expanded applications, shifting paradigms and an improved understanding of host-biomaterial interactions. Acta Biomater 9(2):4948-4955.
3. Brown B N, Ratner B D, Goodman S B, Amar S, & Badylak S F (2012) Macrophage polarization: an opportunity for improved outcomes in biomaterials and regenerative medicine. Biomaterials 33(15):3792-3802.
4. Miron R J & Bosshardt D D (2016) OsteoMacs: Key players around bone biomaterials. Biomaterials 82:1-19.
5. Barbeck M, et al. (2016) Heterogeneity of biomaterial-induced multinucleated giant cells: Possible importance for the regeneration process? J Biomed Mater Res A 104(2): 413-418.
6. Anderson J M & Jones J A (2007) Phenotypic dichotomies in the foreign body reaction. Biomaterials 28(34):5114-5120.
7. Bryers J D, Giachelli C M, & Ratner B D (2012) Engineering biomaterials to integrate and heal: the biocompatibility paradigm shifts. Biotechnol Bioeng 109(8):1898-1911.
8. Xue J, et al. (2014) Transcriptome-based network analysis reveals a spectrum model of human macrophage activation. Immunity 40(2):274-288.
9. Mosser D M & Edwards J P (2008) Exploring the full spectrum of macrophage activation. Nat Rev Immunol 8(12):958-969.
10. Brown B N, Sicari B M, & Badylak S F (2014) Rethinking regenerative medicine: a macrophage-centered approach. Front Immunol 5:510.
11. Murray P J & Wynn T A (2011) Protective and pathogenic functions of macrophage subsets. Nat Rev Immunol 11(11):723-737.
12. Mills C D (2012) M1 and M2 Macrophages: Oracles of Health and Disease. Crit Rev Immunol 32(6):463-488.

13. Brown B N, et al. (2012) Macrophage phenotype as a predictor of constructive remodeling following the implantation of biologically derived surgical mesh materials. Acta Biomater 8(3):978-987.

14. Madden L R, et al. (2010) Proangiogenic scaffolds as functional templates for cardiac tissue engineering. Proc Natl Acad Sci USA 107(34):15211-15216.

15. Brown B N, Valentin J E, Stewart-Akers A M, McCabe G P, & Badylak S F (2009) Macrophage phenotype and remodeling outcomes in response to biologic scaffolds with and without a cellular component. Biomaterials 30(8): 1482-1491.

16. Mokarram N, Merchant A, Mukhatyar V, Patel G, & Bellamkonda R V (2012) Effect of modulating macrophage phenotype on peripheral nerve repair. Biomaterials 33(34): 8793-8801.

17. Guo R, Merkel A R, Sterling J A, Davidson J M, & Guelcher S A (2015) Substrate modulus of 3D-printed scaffolds regulates the regenerative response in subcutaneous implants through the macrophage phenotype and Wnt signaling. Biomaterials 73:85-95.

18. Sussman E M, Halpin M C, Muster J, Moon R T, & Ratner B D (2014) Porous implants modulate healing and induce shifts in local macrophage polarization in the foreign body reaction. Ann Biomed Eng 42(7):1508-1516.

19. Fearing B V & Van Dyke M E (2014) In vitro response of macrophage polarization to a keratin biomaterial. Acta Biomater 10(7):3136-3144.

20. Ho V W & Sly L M (2009) Derivation and characterization of murine alternatively activated (M2) macrophages. Methods Mol Biol 531:173-185.

21. Martinez F O & Gordon S (2014) The M1 and M2 paradigm of macrophage activation: time for reassessment. F1000Prime Rep 6:13.

22. Orenstein S B, Saberski E R, Kreutzer D L, & Novitsky Y W (2012) Comparative analysis of histopathologic effects of synthetic meshes based on material, weight, and pore size in mice. J Surg Res 176(2):423-429.

23. Klinge U, et al. (2002) Impact of polymer pore size on the interface scar formation in a rat model. J Surg Res 103(2):208-214.

24. Borges J & Mano J F (2014) Molecular interactions driving the layer-by-layer assembly of multilayers. Chem Rev 114(18):8883-8942.

25. Ai H, Jones S A, & Lvov Y M (2003) Biomedical applications of electrostatic layer-by-layer nano-assembly of polymers, enzymes, and nanoparticles. Cell Biochem Biophys 39(1):23-43.

26. Macdonald M, Rodriguez N M, Smith R, & Hammond P T (2008) Release of a model protein from biodegradable self assembled films for surface delivery applications. J Control Release 131(3):228-234.

27. Macdonald M L, Rodriguez N M, Shah N J, & Hammond P T (2010) Characterization of tunable FGF-2 releasing polyelectrolyte multilayers. Biomacromolecules 11(8):2053-2059.

28. Keeney M, et al. (2013) Mutant MCP-1 protein delivery from layer-by-layer coatings on orthopedic implants to modulate inflammatory response. Biomaterials 34(38):10287-10295.

29. Shah N J, et al. (2013) Surface-mediated bone tissue morphogenesis from tunable nanolayered implant coatings. Sci Transl Med 5(191):191ra183.

30. Shah N J, et al. (2014) Adaptive growth factor delivery from a polyelectrolyte coating promotes synergistic bone tissue repair and reconstruction. Proc Natl Acad Sci USA 111(35):12847-12852.

31. Shah N J, et al. (2011) Tunable dual growth factor delivery from polyelectrolyte multilayer films. Biomaterials 32(26):6183-6193.

32. Aumsuwan N, Ye S H, Wagner W R, & Urban M W (2011) Covalent attachment of multilayers on poly(tetrafluoroethylene) surfaces. Langmuir 27(17):11106-11110.

33. Shukla S K, Mishra A K, Arotiba O A, & Mamba B B (2013) Chitosan-based nanomaterials: a state-of-the-art review. Int J Biol Macromol 59:46-58.

34. Kong M, Chen X G, Xing K, & Park H J (2010) Antimicrobial properties of chitosan and mode of action: a state of the art review. Int J Food Microbiol 144(1):51-63.

35. Lee C G, et al. (2011) Role of chitin and chitinase/chitinase-like proteins in inflammation, tissue remodeling, and injury. Annu Rev Physiol 73:479-501.

36. den Dekker E, et al. (2008) Monocyte cell surface glycosaminoglycans positively modulate IL-4-induced differentiation toward dendritic cells. J Immunol 180(6):3680-3688.

37. Porta C, Riboldi E, Ippolito A, & Sica A (2015) Molecular and epigenetic basis of macrophage polarized activation. Semin Immunol 27(4):237-248.

38. Tugal D, Liao X, & Jain M K (2013) Transcriptional control of macrophage polarization. Arterioscler Thromb Vasc Biol 33(6):1135-1144.

39. Lawrence T & Natoli G (2011) Transcriptional regulation of macrophage polarization: enabling diversity with identity. Nat Rev Immunol 11(11):750-761.

40. Nadkarni S K, et al. (2007) Measurement of collagen and smooth muscle cell content in atherosclerotic plaques using polarization-sensitive optical coherence tomography. J Am Coll Cardiol 49(13):1474-1481.

41. Jetten N, et al. (2014) Wound administration of M2-polarized macrophages does not improve murine cutaneous healing responses. PLoS One 9(7):e102994.

42. Wynn T A, Chawla A, & Pollard J W (2013) Macrophage biology in development, homeostasis and disease. Nature 496(7446):445-455.

43. Liu Y C, Zou X B, Chai Y F, & Yao Y M (2014) Macrophage polarization in inflammatory diseases. Int J Biol Sci 10(5):520-529.

44. Udpa N, et al. (2013) Effects of chitosan coatings on polypropylene mesh for implantation in a rat abdominal wall model. Tissue Eng Part A 19(23-24):2713-2723.

45. Meyers S R & Grinstaff M W (2012) Biocompatible and bioactive surface modifications for prolonged in vivo efficacy. Chem Rev 112(3):1615-1632.

46. van Bilsen P H, et al. (2004) Ongoing foreign body reaction to subcutaneous implanted (heparin) modified Dacron in rats. J Biomed Mater Res A 68(3):423-427.

47. Liu L, et al. (2008) Reduced foreign body reaction to implanted biomaterials by surface treatment with oriented osteopontin. J Biomater Sci Polym Ed 19(6):821-835.

48. Khandwekar A P, Patil D P, Hardikar A A, Shouche Y S, & Doble M (2010) In vivo modulation of foreign body response on polyurethane by surface entrapment technique. J Biomed Mater Res A 95(2):413-423.

49. Pierce L M, et al. (2009) Long-term histologic response to synthetic and biologic graft materials implanted in the vagina and abdomen of a rabbit model. Am J Obstet Gynecol 200(5):546 e541-548.

50. Brown B N, et al. (2015) Characterization of the host inflammatory response following implantation of prolapse mesh in rhesus macaque. Am J Obstet Gynecol.

51. Sicari B M, et al. (2014) The promotion of a constructive macrophage phenotype by solubilized extracellular matrix. Biomaterials 35(30):8605-8612.

52. A. R. Reeves, K. L. Spiller, D. O. Freytes, G. Vunjak-Novakovic, D. L. Kaplan, Controlled release of cytokines using silk-biomaterials for macrophage polarization, Biomaterials 73 (2015) 272-283.

53. K. L. Spiller, S. Nassiri, C. E. Witherel, R. R. Anfang, J. Ng, K. R. Nakazawa, T. Yu, G. Vunjak-Novakovic, Sequential delivery of immunomodulatory cytokines to facilitate the M1-to-M2 transition of macrophages and enhance vascularization of bone scaffolds, Biomaterials 37 (2015) 194-207.

54. J. Pajarinen, Y. Tamaki, J. K. Antonios, T. H. Lin, T. Sato, Z. Yao, M. Takagi, Y. T. Konttinen, S. B. Goodman, Modulation of mouse macrophage polarization in vitro using IL-4 delivery by osmotic pumps, J. Biomed. Mater. Res. A 103 (4) (2015) 1339-1345.

55. S. B. Goodman, Wear particles, periprosthetic osteolysis and the immune system, Biomaterials 28 (34) (2007) 5044-5048.

56. E. Jamsen, V. P. Kouri, J. Olkkonen, A. Cor, S. B. Goodman, Y. T. Konttinen, J. Pajarinen, Characterization of macrophage polarizing cytokines in the aseptic loosening of total hip replacements, J. Orthop. Res. Off. Publ. Orthop. Res. Soc. 32 (9) (2014) 1241-1246.

57. T. H. Lin, S. Kao, T. Sato, J. Pajarinen, R. Zhang, F. Loi, S. B. Goodman, Z. Yao, Exposure of polyethylene particles induces interferon-gamma expression in a natural killer T lymphocyte and dendritic cell coculture system in vitro: a preliminary study, J. Biomed. Mater. Res. A 103 (1) (2015) 71-75.

58. J. Pajarinen, E. Jamsen, Y. T. Konttinen, S. B. Goodman, Innate immune reactions in septic and aseptic osteolysis around hip implants, J. Long-term Eff. Med. Implants 24 (4) (2014) 283-296.

59. T. H. Lin, J. Pajarinen, T. Sato, F. Loi, C. Fan, L. A. Cordova, A. Nabeshima, E. Gibon, R. Zhang, Z. Yao, S. B. Goodman, NF-kappaB decoy oligodeoxynucleotide mitigates wear particle-associated bone loss in the murine continuous infusion model, Acta Biomater. 41 (1) (2016) 273-281.

60. T. Sato, J. Pajarinen, A. Behn, X. Jiang, T. H. Lin, F. Loi, Z. Yao, K. Egashira, F. Yang, S. B. Goodman, The effect of local IL-4 delivery or CCL2 blockade on implant fixation and bone structural properties in a mouse model of wear particle induced osteolysis, J. Biomed. Mater. Res. A 104 (9) (2016) 2255-2262.

61. A. L. Nolfi, B. N. Brown, R. Liang, S. L. Palcsey, M. J. Bonidie, S. D. Abramowitch, P. A. Moalli, Host response to synthetic mesh in women with mesh complications, Am. J. Obstet. Gynecol. 215 (2) (2016), 206.e1-206.e8.

62. P. Sacerdote, Opioids and the immune system, Palliat. Med. 20 (Suppl. 1) (2006) s9-15.

63. C. Martucci, A. E. Panerai, P. Sacerdote, Chronic fentanyl or buprenorphine infusion in the mouse: similar analgesic profile but different effects on immune responses, Pain 110 (1-2) (2004) 385-392.

64. A. K. McNally, J. M. Anderson, Interleukin-4 induces foreign body giant cells from human monocytes/macrophages. Differential lymphokine regulation of macrophage fusion leads to morphological variants of multinucleated giant cells, Am. J. Pathol. 147 (5) (1995) 1487-1499.

65. J. A. Jones, A. K. McNally, D. T. Chang, L. A. Qin, H. Meyerson, E. Colton, I. L. Kwon, T. Matsuda, J. M. Anderson, Matrix metalloproteinases and their inhibitors in the foreign body reaction on biomaterials, J. Biomed. Mater Res. A 84 (1) (2008) 158-166.

66. R. C. Smith, M. Riollano, A. Leung, P. T. Hammond, Layer-by-layer platform technology for small-molecule delivery, Angew. Chem. Int. Ed. Engl. 48 (47) (2009) 8974-8977.

67. D. Choi, J. Hong, Layer-by-layer assembly of multilayer films for controlled drug release, Arch. Pharm. Res. 37 (1) (2014) 79-87.

68. I. G. Luzina, A. D. Keegan, N. M. Heller, G. A. Rook, T. Shea-Donohue, S. P. Atamas, Regulation of inflammation by interleukin-4: a review of "alternatives", J. Leukoc. Biol. 92 (4) (2012) 753-764.

69. I. G. Luzina, V. Lockatell, N. W. Todd, K. Highsmith, A. D. Keegan, J. D. Hasday, S. P. Atamas, Alternatively spliced variants of interleukin-4 promote inflammation differentially, J. Leukoc. Biol. 89 (5) (2011) 763-770.

70. P. J. Murray, T. A. Wynn, Obstacles and opportunities for understanding macrophage polarization, J. Leukoc. Biol. 89 (4) (2011) 557-563.

71. M. Rath, I. Muller, P. Kropf, E. I. Closs, M. Munder, Metabolism via arginase or nitric oxide synthase: two competing arginine pathways in macrophages, Front. Immunol. 5 (2014) 532.

72. T. A. Wynn, K. M. Vannella, Macrophages in tissue repair, regeneration, and fibrosis, Immunity 44 (3) (2016) 450-462.

73. L. Barron, T. A. Wynn, Fibrosis is regulated by Th2 and Th17 responses and by dynamic interactions between fibroblasts and macrophages, Am. J. Physiol. Gastrointest. Liver Physiol. 300 (5) (2011) G723-G728.

74. D. J. Holt, L. M. Chamberlain, D. W. Grainger, Cell-cell signaling in co-cultures of macrophages and fibroblasts, Biomaterials 31 (36) (2010) 9382-9394.

75. D. J. Holt, D. W. Grainger, Multinucleated giant cells from fibroblast cultures, Biomaterials 32 (16) (2011) 3977-3987.

Various references are cited in this document, which are hereby incorporated by reference in their entireties herein.

The invention claimed is:

1. A kit for remodeling a target tissue, comprising:
   a biomaterial coated with a coating, wherein the coating includes
   (a) at least one polycation layer;
   (b) at least one polyanion layer;
   (c) at least one active agent-containing layer comprising dermatan sulfate and an M2 polarizing active agent, wherein the M2 polarizing active agent is pre-incubated with the dermatan sulfate in a ratio between about 1:10 to about 1:2000 to be complexed, and wherein the at least one polycation layer and the at least one polyanion layer alternate to form a bilayer; and
   instructions for implanting the biomaterial adjacent to the target tissue.

2. The kit of claim 1, wherein the instructions comprise information for implanting the biomaterials to release an effective concentration of the M2 polarizing active agent at a target tissue-biomaterial interface.

3. The kit of claim 1, further comprising additional polycation and polyanion for tuning a number or a composition of the polycation layer, the polyanion layer, the active agent-containing layer, or a combination thereof.

4. The kit of claim 1, wherein the biomaterial is selected from the group consisting of mesh, polypropylene, metal, tissue engineering scaffold, polytetrafluoroethylene, polyethylene, polystyrene, and combinations thereof.

5. The kit of claim 1, wherein polycation in the at least one polycation layer is selected from the group consisting of a polysaccharide, a protein, a synthetic polypeptide, a synthetic polyamine, a synthetic polymer, and combinations thereof.

6. The kit of claim 1, wherein polyanion in the at least one polyanion layer is selected from the groups consisting of a polysaccharide, a protein, a synthetic polypeptide, a synthetic polyamine, a synthetic polymer, and combinations thereof.

7. The kit of claim 1, wherein polycation in the at least one polycation layer is chitosan, and the polyanion in the at least one polyanion layer is the dermatan sulfate.

8. The kit of claim 1, wherein the M2 polarizing active agent is IL-4.

9. The kit of claim 1, wherein the coating is from about 0.5 nm to about 500 µm.

10. The kit of claim 1, wherein the biomaterial comprises a total of about 4 to about 20 bilayers, wherein the bilayers do not contain the M2 polarizing active agent.

11. The kit of claim 1, wherein the coated biomaterial comprises about 20 to about 100 M2 polarizing active agent containing layers.

12. A kit for coating a biomaterial, comprising:
a polycation for coating the biomaterial with a polycation layer;
a polyanion for coating the biomaterial with a polyanion layer;
an M2 polarizing active agent and dermatan sulfate to be incorporated into at least one layer, wherein the M2 polarizing active agent is pre-incubated with the dermatan sulfate in a ratio between about 1:10 to about 1:2000 to be complexed; and
instructions for preparing a coated biomaterial, wherein the coated biomaterial comprises the polycation layer and the polyanion layer that alternate to form at least one bilayer.

13. The kit of claim 12, further comprising the biomaterial to be coated.

14. The kit of claim 13, wherein the biomaterial is selected from the group consisting of mesh, polypropylene, metal, tissue engineering scaffold, polytetrafluoroethylene, polyethylene, polystyrene, and combinations thereof.

15. The kit of claim 12, wherein the polycation and the polyanion are in dry form.

16. The kit of claim 15, further comprising a buffer for creating a polycation solution and a polyanion solution.

17. The kit of claim 12, wherein the polycation and the polyanion are in liquid form.

18. The kit of claim 12, wherein polycation is selected from the group consisting of a polysaccharide, a protein, a synthetic polypeptide, a synthetic polyamine, a synthetic polymer, and combinations thereof.

19. The kit of claim 12, wherein polyanion is selected from the groups consisting of a polysaccharide, a protein, a synthetic polypeptide, a synthetic polyamine, a synthetic polymer, and combinations thereof.

20. The kit of claim 12, wherein the instructions include information for layer by layer coating of the biomaterial using the polycation, the polyanion, the M2 polarizing active agent, and the dermatan sulfate.

* * * * *